United States Patent
Guthrie et al.

(10) Patent No.: US 7,319,014 B2
(45) Date of Patent: Jan. 15, 2008

(54) OVEREXPRESSION, PURIFICATION AND CHARACTERIZATION OF A THERMOLABILE PHOSPHATASE

(75) Inventors: Ellen Guthrie, Andover, MA (US); Theodore Davis, Boxford, MA (US); Jack Benner, II, South Hamilton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 185 days.

(21) Appl. No.: 10/545,905

(22) PCT Filed: Feb. 20, 2004

(86) PCT No.: PCT/US2004/004996

§ 371 (c)(1),
(2), (4) Date: Aug. 17, 2005

(87) PCT Pub. No.: WO2004/076628

PCT Pub. Date: Sep. 10, 2004

(65) Prior Publication Data

US 2006/0252118 A1    Nov. 9, 2006

Related U.S. Application Data

(60) Provisional application No. 60/449,711, filed on Feb. 24, 2003.

(51) Int. Cl.
C12Q 1/42    (2006.01)
C12P 21/06    (2006.01)
C12N 9/16    (2006.01)

(52) U.S. Cl. .......................... 435/21; 435/68.1; 435/196

(58) Field of Classification Search ..................... None
See application file for complete search history.

(56) References Cited

U.S. PATENT DOCUMENTS

| 5,707,853 | A | 1/1998 | Millian |
| 5,773,226 | A | 6/1998 | Millian |
| 5,891,699 | A | 4/1999 | Boulain et al. |
| 6,379,940 | B2 | 4/2002 | Moffett et al. |
| 6,387,634 | B2 | 5/2002 | Moffett et al. |

FOREIGN PATENT DOCUMENTS

| EP | 0 352 894 | 1/1990 |
| EP | 0441252 | 9/1997 |
| EP | 0 780 466 | 6/2001 |
| WO | WO 01/81365 | 11/2001 |

OTHER PUBLICATIONS

International Search Report Jul. 25, 2005.
Reid et al. The Enzymes, vol. IV ch. 17, p. 373 (1971).
Sambrook et al. Molecular Cloning, A Laboratory Manual Sections 1.53-1.72 (1989).
Piesecki et al. Biotechnol. Bioeng. 42: 178-184 (1993).
Bennett, et al. *J. Biol. Chem.*, 271(29): 17006-17012 (1996).
Chen, et al. *Acta Biochimica et Biophysica Sinica*, 28(5): 523-530 (1996).
Rina, et al. *Eur. J. Biochem.*, 267:1230-1238 (2000).
Zhang, et al. *Analytical Biochemistry*,292: 307-310 (2001).
Wenner, et al. *Analytical Biochemistry*, 268: 201-212 (1999).

*Primary Examiner*—Sheridan Swope
(74) *Attorney, Agent, or Firm*—Harriet M. Strimpel

(57) ABSTRACT

Compositions for an alkaline phosphatase and methods for over-expression and purification of thermolabile Antarctic phosphatase (TAP) are provided. Uses for TAP include dephosphorylation of nucleic acids, sugars, peptides and proteins. TAP as described herein has advantages over phosphatases from other sources with respect to thermolability at 65° C. and efficiency of dephosphorylation activity at approximately neutral pH.

1 Claim, 14 Drawing Sheets

PURIFICATION OF TAP
FROM AN *E.coli* STRAIN CONTAINING pN1

TEST INDUCTION OF DIFFERENT TAP CLONES

TEST PURIFICATION OF TAP UNDER NONDENATURING CONDITIONS

TEST PURIFICATION OF TAP FROM CLONE pEGTAP7.4.1 pH STUDY OF TAP ACTIVITY

THE EFFECT OF DIFFERENT SALTS ON ACTIVITY OF TAP

HEAT KILL OF PHOSPHATASE

STABILITY OF TAP AT 37°C AND 25°C

DEOXYNUCLEOTIDASE ACTIVITY OF TAP AND SAP

TAP - dATP

SAP - dATP

ACTIVITY OF TAP ON PYROPHOSPHATE

TAP vs. CIAP ACTIVITY ON PHOSPHORYLATED MYELIN BASIC PROTEIN

| PHOSPHORYLATED RESIDUES | PHOSPHATASE | SPECIFIC ACTIVITY (nmol/min/mg) |
|---|---|---|
| Ser/Thr | TAP | 1910 |
| Ser/Thr | CIAP | 1573 |
| Tyr | TAP | 1053 |
| Tyr | CIAP | 886 |

ACTIVITY OF TAP ON PHOSPHO-PEPTIDES
PHOSPHO-SERINE

ACTIVITY OF TAP ON PHOSPHO-PEPTIDES
PHOSPHO-THREONINE

ACTIVITY OF TAP ON PHOSPHO-PEPTIDES

ASSAY OF TAP ON SUGAR-PHOSPHATES

FIG. 16

PRIMERS FOR PCR OF TAP GENE

FORWARD PRIMER: (SEQ ID NOS:6 AND 7)

```
        NdeI
5' CCCCCCCATATGCATCATCATCATCATCATGTAAAAAAATGAGCCTCAATTAAAAACACCC 3'
            M  H  H  H  H  H  H  V  K  N  E  P  Q  L  K  T  P
```

REVERSE PRIMER: (SEQ ID NO:8)

```
         XhoI
5' GTCAGGTCTTAGCTCGAGTTATTGATTCCAC 3'
```

FIG. 17
SEQUENCE OF TAP
(SEQ ID NOS: 9 AND 10)

```
ATGAAGCTTAAAAAAATTGTTTTTACCCTAATCGCATTAGGTCTATTTTCTTGCAAAACA
 M  K  L  K  K  I  V  F  T  L  I  A  L  G  L  F  S  C  K  T

ACAAGTGTTTTAGTAAAAAAATGAGCCTCAATTAAAAACACCCAAAAATGTTATTCTGTTA
 T  S  V  L  V  K  N  E  P  Q  L  K  T  P  K  N  V  I  L  L

ATTAGTGATGGCGCAGGATTATCACAAATTTCATCTACCTTTTATTTTAAAGAGGGTACT
 I  S  D  G  A  G  L  S  Q  I  S  S  T  F  Y  F  K  E  G  T

CCAAACTACACACAGTTTAAAAAATATTGGCTTGATAAAAACATCCTCTTCCAGAGAAGAT
 P  N  Y  T  Q  F  K  N  I  G  L  I  K  T  S  S  R  E  D

GTAACTGATTCAGCCTCTGGCGCTACTGCTTTTTCCTGTGGTATTAAAACATATAATGCG
 V  T  D  S  A  S  G  A  T  A  F  S  C  G  I  K  T  Y  N  A

GCAATTGGTGTTGCTGATGATTCAACTGCTGTAAAAAGCATTGTGGAAATTGCAGCATTA
 A  I  G  V  A  D  D  S  T  A  V  K  S  I  V  E  I  A  A  L

AACAACATTAAAACAGGAGTTGTTGCAACGTCCTCCATTACACATGCTACGCCTGCAAGT
 N  N  I  K  T  G  V  V  A  T  S  S  I  T  H  A  T  P  A  S

TTTTATGCCCATGCTTTAAACAGAGGCCTAGAAGAAGAAATTGCGATGGATATGACGGAA
 F  Y  A  H  A  L  N  R  G  L  E  E  E  I  A  M  D  M  T  E

TCTGATCTAGACTTTTTTGCTGGAGGCGGTTTAAACTACTTTACCAAGCGTAAAGACAAA
 S  D  L  D  F  F  A  G  G  G  L  N  Y  F  T  K  R  K  D  K

AAAGATGTTTTAGCTATTTTAAAAGGAAATCAATTTACCATAAATACTACTGGATTAACA
 K  D  V  L  A  I  L  K  G  N  Q  F  T  I  N  T  T  G  L  T

GATTTTTCAAGCATTGCATCAAATAGAAAAATGGGTTTTTTATTAGCGGATGAAGCCATG
 D  F  S  S  I  A  S  N  R  K  M  G  F  L  L  A  D  E  A  M

CCTACTATGGAAAAAGGAAGAGGTAATTTTCTATCCGCAGCAACAGATTTAGCCATTCAG
 P  T  M  E  K  G  R  G  N  F  L  S  A  A  T  D  L  A  I  Q

TTTTTAAGTAAAGACAATTCAGCGTTCTTTATTATGAGCGAAGGTTCTCAAATAGATTGG
 F  L  S  K  D  N  S  A  F  F  I  M  S  E  G  S  Q  I  D  W

GGTGGCCATGCAAATAATGCATCCTATTTAATTTCTGAAATTAATGATTTTGACGATGCC
 G  G  H  A  N  N  A  S  Y  L  I  S  E  I  N  D  F  D  D  A

ATTGGCACTGCTTTGGCTTTCGCTAAAAAAGATGGTAATACATTGGTTATTGTAACTTCT
 I  G  T  A  L  A  F  A  K  K  D  G  N  T  L  V  I  V  T  S

GACCATGAAACTGGAGGTTTTACATTGGCTGCCAAAAAAAATAAAAGAGAAGATGGTAGT
 D  H  E  T  G  G  F  T  L  A  A  K  K  N  K  R  E  D  G  S

GAGTATAGTGATTATACAGAGATCGGACCTACTTTTTCTACTGGAGGGCATTCTGCAACC
 E  Y  S  D  Y  T  E  I  G  P  T  F  S  T  G  G  H  S  A  T

TTAATTCCTGTTTTTGCTTACGGCCCTGGATCAGAAGAATTTATTGGAATCTATGAAAAC
 L  I  P  V  F  A  Y  G  P  G  S  E  E  F  I  G  I  Y  E  N

AATGAAATTTTTCATAAAAATATTAAAAGTGACAAAGTGGAATCAATAAACATAACTAAGA
 N  E  I  F  H  K  I  L  K  V  T  K  W  N  Q  *
```

OVEREXPRESSION, PURIFICATION AND CHARACTERIZATION OF A THERMOLABILE PHOSPHATASE

CROSS REFERENCE

This application is a § 371 application of international application number PCT/US04/04996 filed on Feb. 20, 2004, which claims priority from U.S. provisional application number 60/449,711 filed on Feb. 24, 2003, herein incorporated by reference.

BACKGROUND

Purified phosphatases are used by molecular biologists to remove phosphate groups from linearized DNA, RNA, nucleotides and proteins in vitro. Removal of both 5'-terminal phosphate residues from a linearized DNA vector prevents recircularization of the vector DNA in a ligation reaction because DNA ligase catalyzes the formation of a phosphodiester bond between adjacent nucleotides only if one nucleotide contains a 5'-phosphate and the other a 3'-hydroxyl group. However, foreign DNA segments with 5'-terminal phosphates can be ligated efficiently into the dephosphorylated vector to give an open circular molecule containing two nicks that can easily be transformed into competent cells.

Several different phosphatases have been developed for removal of phosphate groups from biological molecules, and each has its own advantages and disadvantages. The first phosphatase to be used for this purpose was Bacterial Alkaline Phosphatase (BAP) purified from *Escherichia coli* (*E. coli*). BAP has the advantage of having good activity against all types of DNA ends. However, it is difficult to remove from the reaction as it is very resistant to heat and detergents (Sambrook, et al., *Molecular Cloning, A Laboratory Manual* Sections 1.53-1.72 (1989)). A mutant BAP has been prepared (U.S. Pat. No. 5,891,699, EP Patent No. 0441252) which reportedly had increased thermostability. Calf Intestinal Alkaline Phosphatase (CIP or CIAP) is another phosphatase that has been extensively used in molecular biology techniques (U.S. Pat. Nos. 5,773,226 and 5,707,853). CIAP is not as active on DNA as BAP, but it is slightly easier to remove from a reaction requiring the use of either Proteinase K treatment followed by phenol:chloroform extractions or a heat step in the presence of EDTA followed by a phenol:chloroform extraction (Sambrook, et al., supra (1989)). More recently a phosphatase isolated from Arctic shrimp *Pandalus borealis* (SAP) (U.S. Pat. Nos. 6,387,634 and 6,379,940) has proved easier to use. It has good activity against all types of DNA ends like BAP, but it is reported to have the advantage that it is easily removed from the reaction by heat inactivation at 65° C. for 15 minutes (Amersham Bioscience, Piscataway, N.J.).

Other reports have occurred in the literature for other thermolabile phosphatases including one purified from a psychrophilic strain TAB5 isolated from Antarctica referred to as Thermolabile Antarctic Phosphatase (TAP) (Rina, et al., *Eur. J. Biochem.* 267:1230-1238 (2000)). Advantages of TAP over other phosphatases include heat lability and high specific activity. Rina, et al. reported that this phosphatase had a specific activity of 1650 units/mg of protein for p-nitrophenyl phosphate (pNPP) substrate which was significantly higher than the activity of any other known phosphatase. However, the protein produced by the clone reported by Rina, et al., (supra (2000)) had a number of problems associated with overexpression and purification. For example, the purification protocol described by Rina, et al., (supra (2000)) requires multiple ultracentrifugation steps to extract the TAP from cell membranes with which it was apparently associated. This protocol is not suited for large scale manufacture (for example, manufacturing protocols involving production of 300 g or more of cell paste). In addition, overexpressing the TAP gene using the protocol described in Rina, et al., resulted in yields of the enzyme that were very low and consequently not cost effective for large scale manufacture.

SUMMARY

Present embodiments of the invention provide an alkaline phosphatase with increased heat lability at neutral pH and enhanced activity and a hydrophilic leader sequence at the N-terminal end of the protein. The hydrophilic leader sequence may be an oligopeptide, for example, an oligopeptide with a net positive charge such as a His tag. Advantages of this phosphatase include the ability to eliminate its activity by raising the temperature to a level at which other reactants and products remain unaffected. An example of a phosphatase having these properties is TAP which is described in detail in the examples. Although the method described herein relies on the presence of a hydrophilic leader sequence, such as His tag, fused to the N-terminal end of the protein, the protein is preferably not purified using a nickel column because the nickel column buffer had an adverse effect on activity. Nonetheless, the presence of the hydrophilic leader sequence surprisingly enhanced yields during column purification using other column compositions.

In an embodiment of the invention, a truncated enzymatically active TAP is provided in which the truncation corresponds to a deletion of a signal sequence, the phosphatase having a C-terminal and N-terminal end, wherein the N-terminal end is covalently linked to a hydrophilic leader sequence, such as a positively charge oligopeptide, for example, a His tag. The truncated TAP can be substantially inactivated at about 65° C. and in less than 15 minutes. In particular, the activity of the truncated TAP is substantially stable in Tris-HCL at a pH greater than pH 6 more particularly at about pH 7.4.

In addition, a DNA is described that encodes TAP (also listed in GenBank Y18016) but which lacks some or all of the signal sequence associated with the naturally occurring TAP gene. The DNA may further include sequences that encode a plurality of His amino acids preferably at the N-terminal of the expressed TAP gene. This DNA may be expressed in a vector under control of a strong promoter, for example, the T7 promoter.

In a preferred embodiment, vectors are provided that contain the DNA described above. An example of these vectors is pEGTAP7.4.1. In additional embodiments of the invention, host cells are provided which have been transformed with at least one vector. In the examples, the host cell is *E. coli* although the use of other host cell types is not excluded.

In additional embodiments of the invention, a formulation of TAP is provided which is substantially stable at 37° C. in a buffer which includes Tris-HCL, $MgCl_2$, DTT and glycerol and more particularly where the pH is about 7.4.

In an embodiment of the invention, a method is provided for overexpressing TAP, that includes (a) operably linking to a T7 promoter, a truncated TAP gene fused to a sequence for expressing a hydrophilic oligopeptide, such as a His tag; (b) transforming a host cell; and (c) overexpressing TAP. In further embodiments, the TAP gene encodes a TAP protein having an N-terminal and a C-terminal end, wherein the TAP protein is truncated at the N-terminal end, the truncation corresponding to a signal sequence, the N-terminal end having the hydrophilic oligopeptide attached hereto.

In an additional embodiment of the invention, a method is provided for obtaining a purified TAP, that includes (a) obtaining a transformed host cell as described above; (b) disrupting the host cells to yield a soluble fraction; and (c) purifying TAP from the soluble fraction. Moreover, the method may additionally include a column separation wherein the TAP is eluted from the column. In this context, purification refers to an increase in the percentage of TAP protein relative to total protein in the disrupted cell mixture. For example, purification may be achieved when the percentage of TAP protein is more than 5% of the total protein in the mixture. Preferably, the percentage of TAP protein may be more than 50%, 80% or 90% of the total protein. In a particular embodiment, the percentage of TAP protein is purified to about 95% of the total protein.

In an additional embodiment of the invention, a method is provided for assaying for TAP activity, that includes: (a) adding TAP to a substrate in a buffer at about pH 5.5-7.0; and (b) determining the amount of phosphate removed from the substrate in a defined time and at a defined temperature to determine TAP activity. In a preferred embodiment, the buffer includes $ZnCl_2$ and $MgCl_2$ salts. More particularly the buffer is Bis-Tris Propane.

In an additional embodiment, a method of dephosphorylating a phosphorylated substrate is provided that includes adding TAP to the substrate in a buffer at pH 5.5-7.0 and causing an amount of phosphate to be removed from the substrate in a defined time and at a defined temperature.

The substrate may be a nucleic acid or a terminal nucleotide on a nucleic acid, a sugar phosphate, or a phosphorylated peptide or protein.

BRIEF DESCRIPTION OF THE DRAWINGS

FIG. 16 shows the sequence of the forward primer (SEQ ID NO:6) and the reverse primer (SEQ ID NO:8) used to PCR a 1.1 kb fragment from the pN1 plasmid. The expected N-terminal amino acid sequence of the protein (SEQ ID NO:7) resulting from expression from the cloned PCR fragment is indicated below the sequence of the forward primer. The NdeI and XhoI cloning sites contained within the primers are also indicated.

FIG. 17 shows the DNA (SEQ ID NO:9) and amino acid sequence (SEQ ID NO:10) of the intact TAP gene. Indicated in the box is the start of the protein as determined by N-terminal sequence analysis (Rina, et al., supra). Arrows indicate the location at which the PCR primers used to clone the truncated gene would anneal.

DETAILED DESCRIPTION OF THE EMBODIMENTS

TAP gene has been isolated and cloned (pN1) by Rina, et al., and the DNA sequence has been published. However, when attempts were made to overexpress and purify TAP from this clone using the published protocol, a number of problems were encountered including obtaining insufficient amounts of purified enzyme for reagent purposes and the need for multiple ultracentrifugation steps to separate the enzyme from membrane fragments with which it was associated. A protocol is provided herein in which the TAP gene is reliably overexpressed to provide yields of enzyme that are cost effective for large scale manufacture. Furthermore, a purification protocol has been developed that avoids the need for multiple ultracentrifugation steps and is suited for large scale manufacture. Uses for TAP have been established for removing phosphates from nucleic acids, peptides, and sugars. Other substrates which may act as a substrate for TAP are those described by Reid and Wilson in "The Enzymes" vol IV (1971) ch 17, p 373.

In a preferred embodiment, "sugars" here refer to monosaccharides, oligosaccharides or polysaccharides. Sugars include any pentose, hexose or heptulose compound. A phosphate may be cleaved using TAP from any carbon in the sugar wherever the phosphate or phosphates are positioned irrespective of whether the phosphate is an alpha or beta isomer. Examples of some sugar phosphates are provided at the web site http://www.arabidopsis.org. Examples of sugar phosphates include: phosphates of mannose, glucose, fucose, galactose, N-acetylgalactosamine, N-acetylglucosamine, xylose, and rhamnose.

Figure 1:
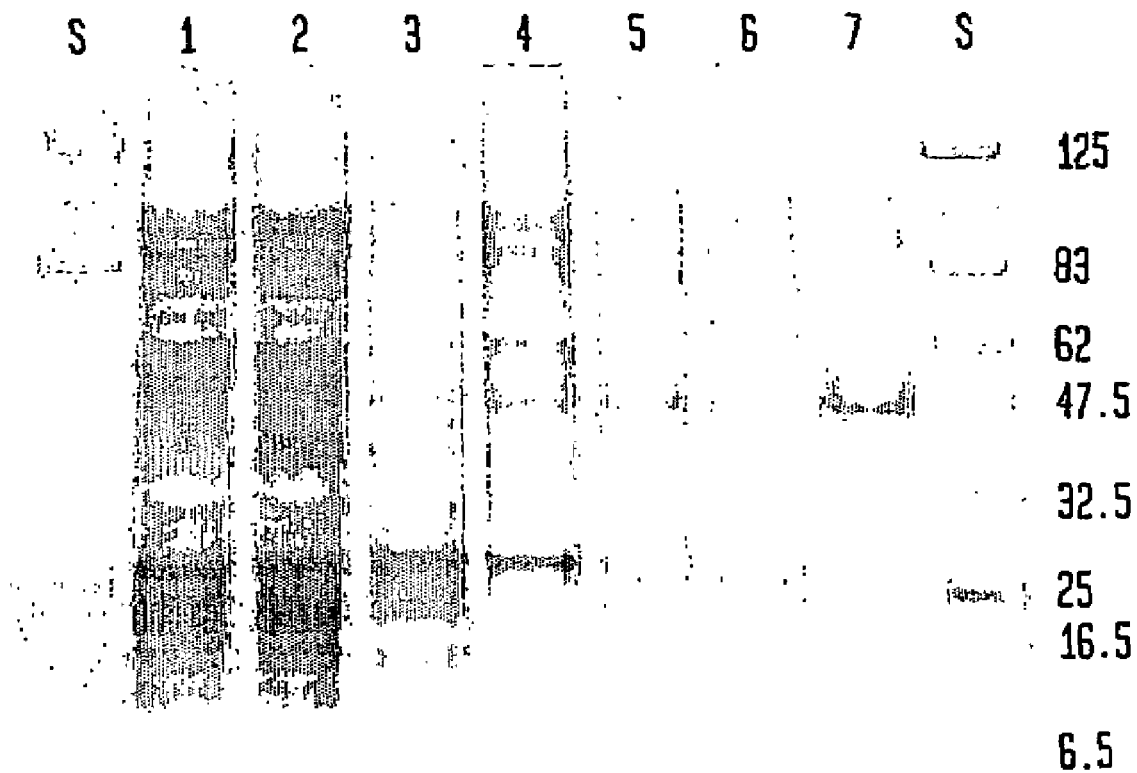
FIG. 1 shows the result of purification of TAP from an *E. coli* strain containing pN1. Lanes 1 through 6 are sequential steps in a purification. Lane 1 is total crude extract after induction. Lane 2 is the solublized membrane fraction. Lane 3 is flow through from a DEAE column. Lane 4 is pooled fractions from a Q-sepharose column. Lane 5 is flow through from a HiTrap S column. Lane 6 is flow through from a Hydroxyapatite column. Lane 7 is purified TAP obtained from the pNI clone. Molecular weight standards (S) are denoted in kD. The band corresponding to 47.5 kD in lane 7 represents substantially purified TAP.

Purification of TAP from ER2575 (ER2566 pLysS) containing the pN1 plasmid was attempted using modifications of the published protocol to improve yield and ease of purification. The transformed *E. coli* strain was grown and induced and the phosphatase was purified as described in Rina, et al. (supra), with the following exceptions. After the soluble membrane fraction was isolated by ultracentrifugation, the proteins were dialyzed in buffer A (20 mM Tris pH 7.6, 10 mM $MgCl_2$, 50 mM NaCl, 0.2% Triton X-100) then loaded onto a DEAE column which had been equilibrated with buffer A. The flow-through which had the phosphatase activity as determined with a pNPP assay was loaded on to a Q-sepharose column as described in Rina, et al. The pooled fractions from the Q-sepharose column were dialyzed in buffer B (Potassium phosphate buffer pH 6.6, 25 mM NaCl, 10 mM $MgCl_2$) and loaded on a Hi-trap SP column which had been equilibrated in buffer B. The flow-through which had the phosphatase activity was dialyzed in buffer C (Potassium phosphate buffer pH 7.2, 50 mM NaCl, 10 mM $MgCl_2$) and loaded onto a hydroxyapatite column which had been equilibrated with buffer C. The phosphatase activity flowed through. Samples from each step were run on a 10-20% Tris tricine PAG (Invitrogen Corp., Carlsbad, Calif.) and stained with Coomassie Brilliant Blue. As can be seen in FIG. 1, the yield of phosphatase in lanes 1-6 was disappointing.

Figure 2:
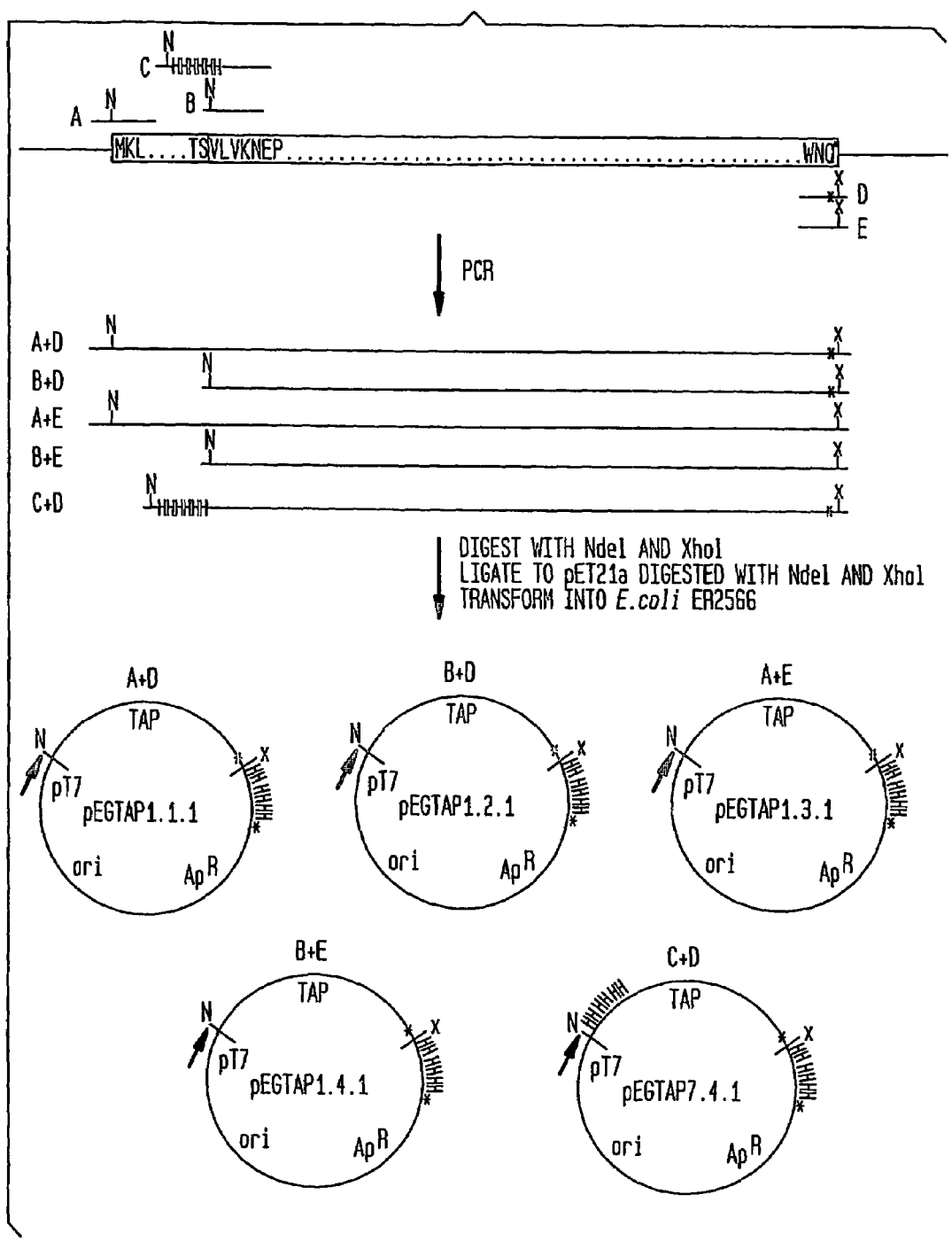
FIG. 2 shows a schematic diagram of the steps used to construct vectors for over-expressing the TAP gene. The rectangle at the top of the figure is a schematic drawing of the gene for TAP including an N-terminal and C-terminal portion of the corresponding expression product of the gene. At the N-terminal end, the location of the methionine start codon and the region around the processing site encoding the hypothesized signal sequence is shown. At the C-terminal end, amino acids of the gene product are shown with the stop codon marked by an asterisk. Primers used in PCR amplification of the TAP gene are drawn above (not to scale) (for the forward primers A, B and C) and below (for the reverse primers D and E) the rectangle at the site at which each primer hybridizes to the TAP gene. The N and X above the primers show engineered cleavage sites for the restriction endonucleases NdeI or XhoI. Primer C shows 6H's following the NdeI site. These correspond to 6 codons encoding histidine inserted downstream of and adjacent to the methionine start codon in the primer to create an N-terminal His-tag fusion with TAP. The next set of lines following "PCR" indicate the resulting products produced by using the pairs of primers indicated. As above, the asterisk indicates a stop codon and the 6H's refer to 6 histidine codons. 5 different plasmid are shown which were created by inserting PCR products into pET21a. pEG-TAP1.1.1 encodes for intact TAP with no His-tag. pEG-TAP1.2.1 encodes for truncated TAP with no His-tag. pEG-TAP1.3.1 encodes for intact TAP with a C-terminal His-tag. pEGTAP1.4.1 encodes for truncated TAP with a C-terminal His-tag. In a later experiment pEGTAP7.4.1 was constructed to encode truncated TAP with an N-terminal His-tag.

With the disappointing results obtained using the above protocols, alternative approaches were investigated that involved cloning the TAP gene as described in FIG. 2.

Specifically, the TAP gene was cloned directly behind a strong promoter (T7 promoter) and attached a His-tag (affinity tag) to facilitate purification. The His-tag sequence shown in FIGS. 13 and 14 has six histidines fused to the N-terminal end of the protein (5' end of the gene). However, this number of histidines is not critical. The number of histidines in the tag may be as few as three or as many as desired in excess of six to achieve the purpose described herein. Several different constructs were made. In two constructs, the TAP gene was truncated by removing a putative signal sequence consisting of 22 amino acids at the N-terminal end of the protein adjacent to the methionine start codon. A C-terminal His-tag was added to form a fusion protein with the truncated phosphatase for one clone but not for another. For example, pEGTAP1.4.1 had a His-tag while pEGTAP1.2.1 did not. In two other constructs, the gene retained the putative signal sequence and either additionally contained a C-terminal His-tag (pEGTAP1.3.1) or not (pEG-TAP1.1.1) (FIG. 2).

Five different plasmids are shown in FIG. 2 which were created by inserting PCR products into pET21a (Example I, FIGS. 2, 11 and 12). pEGTAP1.1.1 encodes for intact TAP with no His-tag. pEGTAP1.2.1 encodes for truncated TAP with no His-tag. pEGTAP1.3.1 encodes for intact TAP with a C-terminal His-tag. pEGTAP1.4.1 encodes for truncated TAP with a C-terminal His-tag. pEGTAP7.4.1 encodes truncated TAP with an N-terminal His-tag.

Figure 3:
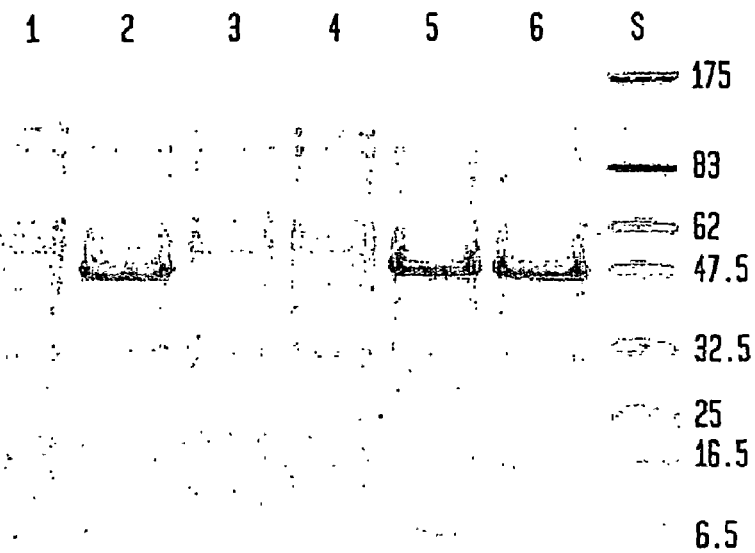
FIG. 3 shows an SDS-PAGE analysis of TAP produced from different clones in which the TAP gene is either truncated or not truncated in the presence or absence of a His-tag. "Test" purification refers to a sample size of less than 1 ml. Lane 1 is the soluble crude extract from clone pEGTAP1.1.1 with the intact TAP gene and with no His-tag. Lane 2 is the soluble crude extract from clone pEGTAP1.2.1 with the truncated TAP gene with no His-tag. Lanes 3 and 4 are soluble crude extracts from two different isolates of the clone pEGTAP1.3.1 with the intact TAP gene fused to a His-tag. Lanes 5 and 6 are soluble crude extracts from two different isolates of the clone pEGTAP1.4.1 with the truncated TAP gene fused to a His-tag. Molecular weight standards (S) are denoted in kD. Those clones having a truncated TAP gene (lanes 2, 5 and 6) provided the strongest bands corresponding to TAP.
Figure 4:
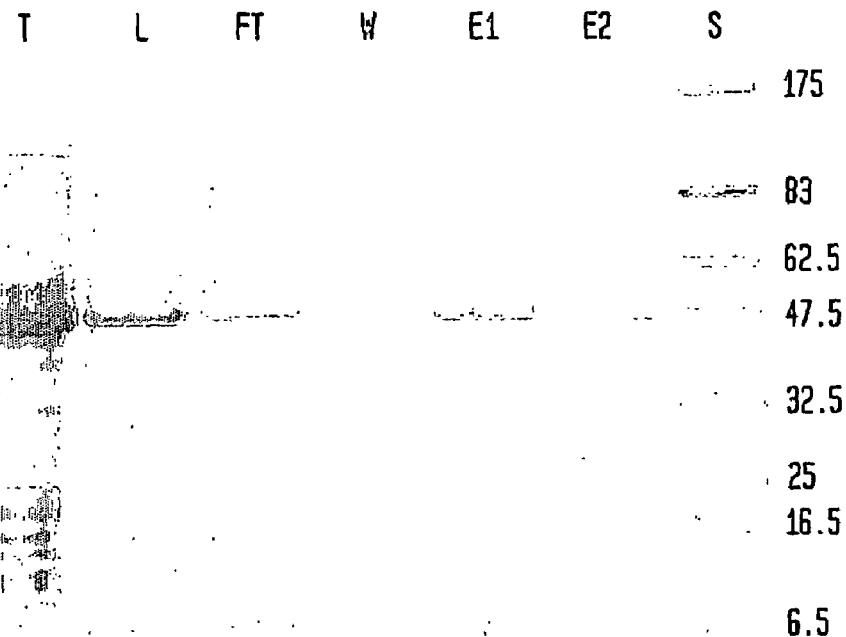
FIG. 4 shows SDS-PAGE analysis of soluble TAP purified under non-denaturing conditions from an *E. coli* (ER2566) clone containing the truncated gene with a C-terminal His-tag (pEGTAP1.4.1). 10 µl samples of the total crude extract (T), the clarified crude extract (load) (L), the flow-through (FT) from the Ni-NTA spin column (Qiagen, Studio City, Calif.), the wash from the Ni-NTA spin column (W) and the first and second samples eluted from the Ni-NTA spin column with the elution buffer (E1 and E2) were run on a 10-20% Tris tricine PAG (Invitrogen Corp., Carlsbad, Calif.) and stained with Coomassie Brilliant Blue. Molecular weight standards (S) denoted in kD.

Plasmids containing the intact TAP gene with the putative signal sequence, with or without the His-tag at the C-terminal end, failed to produce any obvious soluble phosphatase on SDS-PAGE after induction (FIG. 3, lanes 1, 3 and 4). However, those plasmids constructed without the putative signal sequence either with or without the His-tag produced a very strong band of the correct size on SDS-PAGE (FIG. 3, lanes 2, 5 and 6). However, problems occurred during purification of the protein. The transformed host cell ER2566 containing pEGTAP1.4.1 (truncated TAP and C-terminal His) produced predominantly insoluble TAP in non-denaturing conditions (FIG. 4). Purification was attempted under denaturing conditions followed by refolding of the denatured phosphatase. However, this approach yielded relatively small amounts of active enzyme. E. coli ER2566 containing pEGTAP1.2.1 (truncated TAP with no His-tag) produced soluble TAP, however, the protein failed to bind to most columns.

To overcome the above problems, a fifth clone was constructed in which a sequence encoding His-tag was placed at the N-terminal end instead of the C-terminal end of the TAP gene (pEGTAP7.4.1) (FIG. 2). This construct produced good yields of TAP in the soluble fraction (FIG. 5) which could be readily purified without multiple ultracentrifugation steps (Example II). Specifically, the presence of His-tag at the N-terminal end of the phosphatase enabled purification to near homogeneity on only 2 or 3 columns not including a nickel column. While not wishing to be limited by theory, it appears that the primary use of the His-tag was to facilitate production of soluble phosphatase rather than as an affinity tag.

Figure 10:
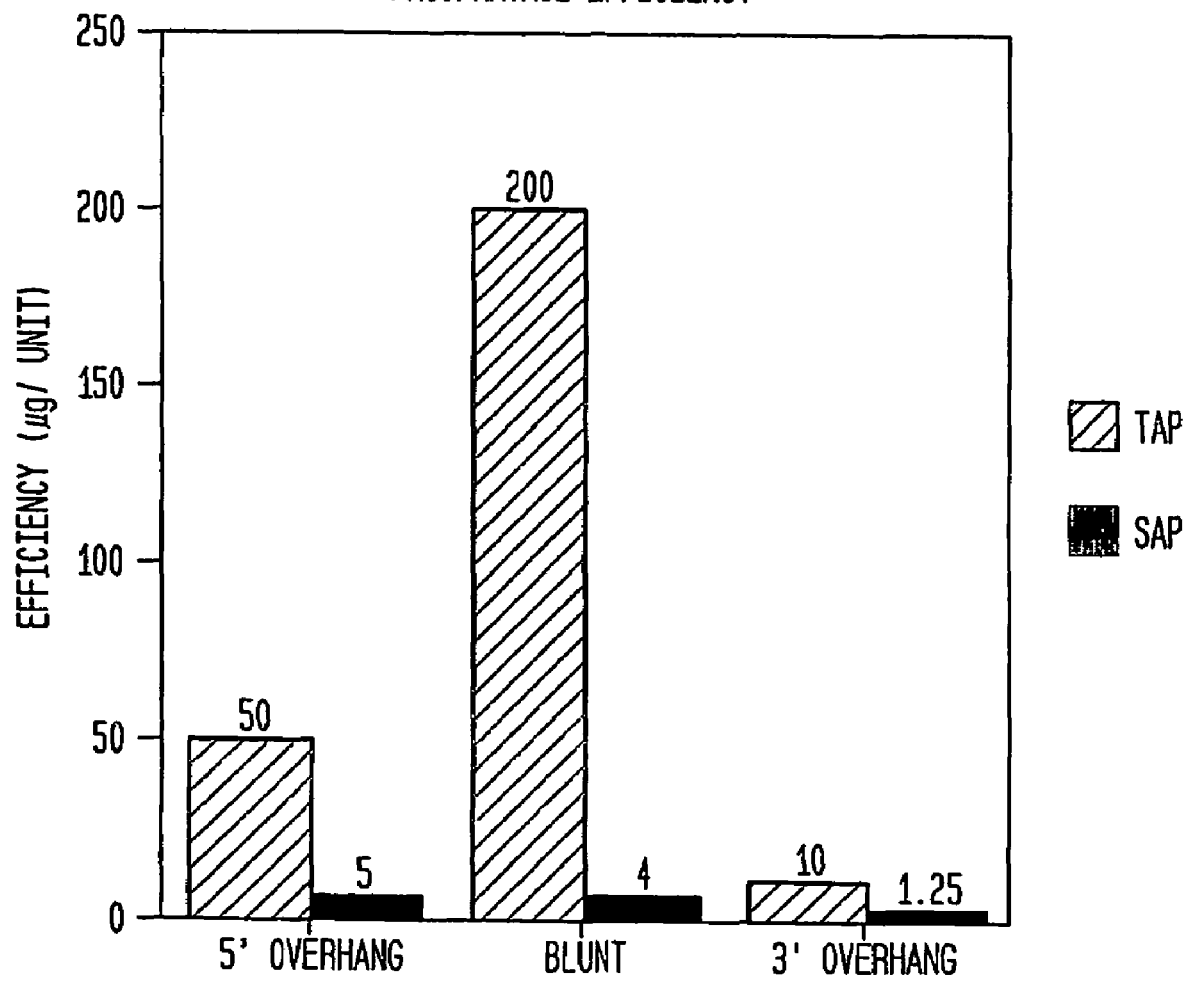
FIG. 10 shows a comparison of the efficiency of TAP to SAP in the removal of phosphate groups from different types of DNA termini: 5' overhang, blunt ends and 3' overhang were tested. These ends were produced by digestion of the vector with HindIII, EcoRV and PstI respectively.

The activity of the TAP phosphatase prepared by the above method (Example I and II) was compared with SAP and CIAP phosphatase activity by means of assays employing DNA and protein substrates. (Example VII) and TAP was found to have enhanced activity. For example, linear DNA dephosphorylation activity of TAP and SAP was determined using a phosphate release assay described in Example VII, for 5' overhangs', 3' overhangs and blunt ends of DNA. When the dephosphorylation of these different structures were compared using identical pNPP unit amounts, TAP proved to be consistently more efficient than SAP (FIG. 10).

Figures 12, 13:
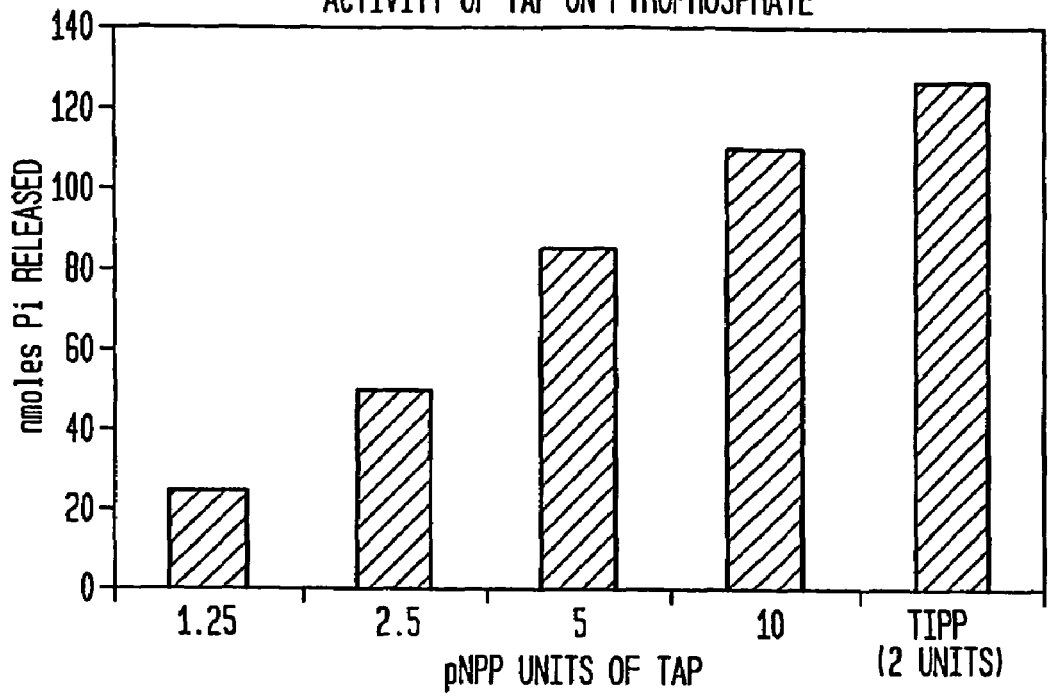
FIG. 12 shows the release of inorganic phosphate from pyrophosphate by TAP. Increasing amounts of TAP were added to each reaction mix containing 0.32 mM sodium pyrophosphate. Inorganic phosphate was measured essentially by the method of Heinonen and Lahti (Heinonen, J. K. and Lahti, R. J. "A new and convenient calorimetric determination of inorganic orthophosphate and its application to the assay of inorganic pyrophosphatase." *Anal. Biochem.* 113(2): 313-7, 1981) by comparison to known phosphate standards. Thermostable inorganic pyrophosphate (TIPP) was used in a parallel reaction to demonstrate equivalence. The results shown are for a 10 minute assay at 37° C. for TAP and at 75° C. for TIPP.
FIG. 13 provides a table showing the specific activity of TAP as compared to CIAP on phosphorylated myelin basic protein.

TAP is also able to remove phosphate groups from serine/threonine and tyrosine residues on phosphorylated proteins as efficiently as CIAP (Example VII, FIG. 13).

Figure 8:
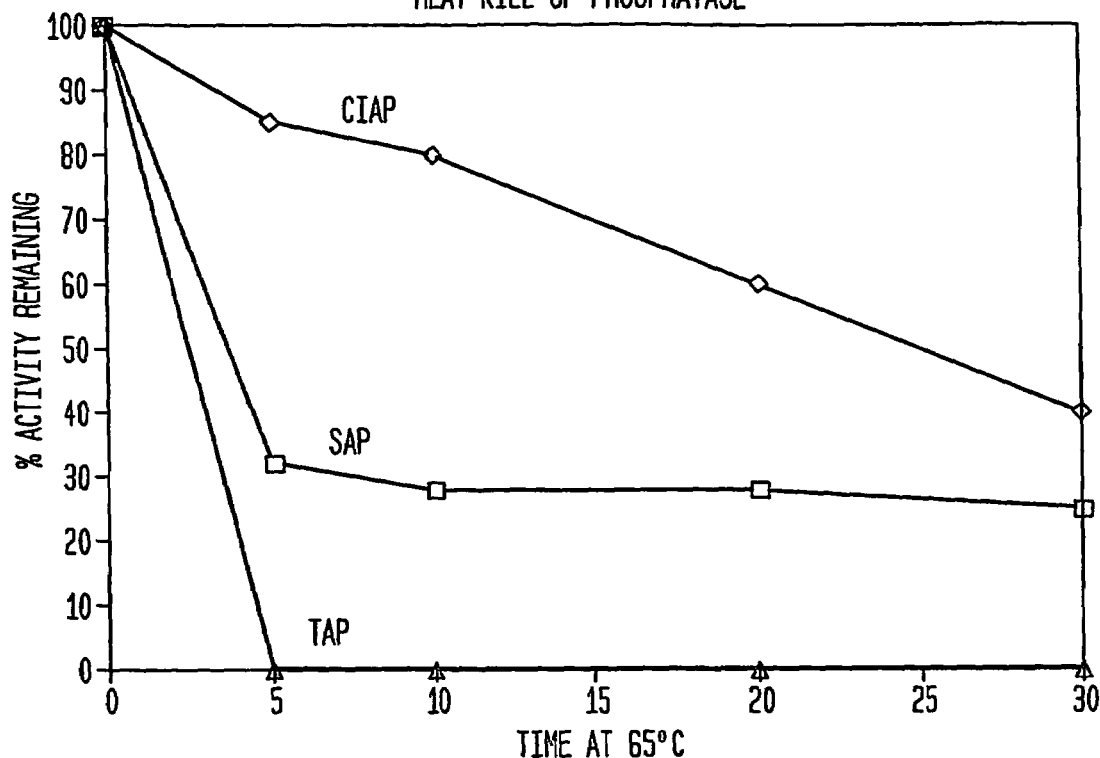
FIG. 8 shows a comparison of the thermolability of CIAP, SAP and TAP. Each enzyme was incubated in the presence of DNA at 65° C. for up to 30 minutes. Samples were taken at different time points during the incubation and were assayed for activity with pNPP.

In addition to increased activity of TAP compared with other phosphatases, TAP was found to have enhanced thermolability (Example IV, FIG. 8). When the heat lability of CIAP, SAP and TAP was compared, it was found that TAP had lost 98% of its activity after 5 minutes at 65° C. compared with SAP which had lost 70% activity and CIAP which had lost only 10% of its activity at this temperature.

In other embodiments of the invention, $ZnCl_2$ and $MgCl_2$ were found to enhance the activity of the phosphatase (Example III). The activity of TAP was optimized at a pH of about 5.5-7.0, for example, using Bis-Tris Propane buffer (Example III).

The present invention is further illustrated by the following Examples. These Examples are provided to aid in the understanding of the invention and are not construed as a limitation thereof.

The references cited above and below are hereby incorporated by reference herein.

EXAMPLES

Example I

Construction and Expression of a TAP His-tag Fusion Gene

Figure 5:
FIG. 5 shows the result of a purification protocol similar to that used in FIG. 4 except that the clone analyzed was ER2566 (pEGTAP7.4.1). Also, instead of running the total cell extract on the gel, the pellet resulting from spinning the crude extract was resuspended and run as insoluble pellet (P). 10 µl of pellet (P), soluble load (L), flow through from Ni-NTA spin column (FT), wash from Ni-NTA spin column (W), elutions from Ni-NTA spin column with imidazole (E) and molecular weight standard (S) denoted in kD were run on a 10-20% Tris tricine PAG and stained with Coomassie Brilliant Blue.

The truncated phosphatase gene derived from an unclassified Antarctic strain TAB5 was cloned with an N-terminal 6-histidine residue tag. Briefly, a 1.1 kb fragment was amplified by PCR from the recombinant plasmid pN1 (Rina, et al., *Eur. J. Biochem.* 267:1230-1238 (2000)). The forward primer (FIG. 2 primer C), in addition to containing the sequence homologous to the 5' end of the gene without the putative signal sequence (63 bp) (FIGS. 16 and 17), contained the NdeI restriction site as part of the ATG start and 6 codons encoding for 6 histidine residues placed between the ATG start and the first codon of the truncated phosphatase gene (FIGS. 16 and 17). The reverse primer (FIG. 2 primer D), in addition to containing the sequence reverse complementary to the 3' end of the gene, contained an XhoI restriction site immediately downstream of the TAA stop codon (FIGS. 16 and 17). Once amplified, the 1.1 kb fragment was digested with NdeI and XhoI and ligated into the T7 expression vector pET21a (Novagen, Madison, Wis.) similarly digested with NdeI and XhoI (Sambrook, et al., *Molecular Cloning, A Laboratory Manual*, Sections 1.53-1.72 (1989)). The resulting ligation was transformed into the *E. coli* strain ER2688 (New England Biolabs, Beverly, Mass.). Plasmids from the transformation were isolated and characterized by restriction mapping and DNA sequencing and when characterized proved to contain an insert of the correct size and sequence. The plasmid constructs were transformed into *E. coli* strain ER2566 (New England Biolabs, Beverly, Mass.) for expression of the phosphatase gene from the T7 promoter. pEGTAP7.4.1 was found to provide the best yield and purification profile (FIGS. 3-5).

Example II

Production and Purification of the TAP His-tag Fusion Protein (a) Small Scale Purification of TAP ER2566 (pEGTAP7.4.1) was grown overnight at 30° C. from an isolated colony in 5 ml Rich Broth ((10 g Tryptone (Difco Laboratories, Livonia, Mich.), 5 g Yeast Extract (Difco Laboratories, Livonia, Mich.), 5 g NaCl ph to 7.2 with NaOH per liter)) with 100 mg/ml carbenicillin. 3 ml of the overnight culture was used to inoculate 300 ml of Rich Broth with 100 mg/ml carbenicillin. The culture was grown at 30° C. to mid log (Klett 70) and chilled on ice, induced with 0.4 mM isopropyl-β-D-thiogalactoside (IPTG) and grown at 15° C. for 20 hours. 35 ml of cells were harvested by centrifugation at 8000 rpm for 10 minutes at 4° C. The supernatant was removed, the cell pellet was weighed and placed at −20° C. for 2 hours. The pellet was thawed on ice and the cells were resuspended in 1 ml lysis buffer (50 mM $NaH_2PO_4$, 300 mM NaCl, 10 mM imidazole pH 8.0). Lysozyme was added to 1 mg/ml and the sample was incubated on ice for 30 minutes. Following incubation the cells were broken by sonication on ice for 6 times at 10 seconds each time with a 1 minute rest half way through. The crude extract was spun at 14,000 rpm for 20 minutes at 4° C. to remove any unbroken cells and any other insoluble material to generate a clarified crude extract. 0.6 ml of the clarified crude extract was loaded on to a Ni-NTA spin column which had been equilibrated with 0.6 ml lysis buffer. The sample was centrifuged at 700×g for 2 min. The flow-through was removed and the column was washed with 2×0.6 ml wash buffer (50 mM $NaH_2PO_4$, 300 mM NaCl, 20 mM imidazole pH 8.0). The protein was eluted with 2×0.2 ml elution buffer (50 mM $NaH_2PO_4$, 30 mM NaCl, 250 mM imidazole pH 8.0). 10 μl of each step were analyzed on SDS-PAGE. The results for pEGTAP7.4.1 are shown in FIG. 5.

(b) Large Scale Purification of TAP from pEGTAP7.4.1 in ER2566

E. coli strain ER2566 harboring the pEGTAP7.4.1 plasmid was grown at 25° C. in 2000 ml Fermentation Rich Broth (500 g Amberex yeast extract (Sensient Technologies, Milwaukee, Wis.), 1 kg CE90MS Tryptone (Marcor Development Corp., Carlstadt, N.J.), 27 g NaOH, 10 g ampicillin, 5.5 g polypropylene glycol antifoam agent (Arco Chemical Co., South Charleston, W. Va.) per 100 liters) at 25° C. This culture was used to inoculate 100 liters of Fermentation Rich Broth. The cells were grown aerobically at 25° C. for 5 hours until they reached a Klett of 70. The fermentor was then cooled to 15° C. and IPTG was added to a final concentration of 0.3 mM when the Klett reached 90. The cells were then grown aerobically at 15° C. for a further 17 hours, reaching stationary phase with a final Klett of 305. One 100 liter fermentation was required to harvest 321 grams of wet cell pellet. The 321 gram cell pellet was suspended in 963 ml buffer A (20 mM Potassium phosphate buffer (pH 7.4), 50 mM NaCl, 5% Gycerol) and passed through a Gaulin homogenizer at ~12,000 psig. The lysate was centrifuged at ~13,000×G for 40 minutes and the supernatant collected (1150 ml).

The supernatant solution was applied to a 500 ml Heparin Hyper-D column (Ciphergen Biosystems, Inc., Fremont, Calif.) equilibrated in buffer A. A 1.0 L wash of buffer A was applied, then a 2 L gradient of NaCl from 0.05 M to 1 M in buffer A was applied and fractions of 50 ml were collected. Fractions were assayed for phosphatase activity by incubating samples with 0.1 M pNPP in 1M diethanolamine/HCL buffer (pH 8.5) containing 10 mM $MgCl_2$. Reactions were carried out at 37° C. for 1-5 minutes and activity was measured as generation of yellow color spectrophotometrically at 405 nm. Phosphatase activity eluted from 0.05-0.35 M NaCl.

The Heparin Hyper-D column fractions containing the phosphatase activity were pooled, then dialyzed against buffer A overnight. 100 ml of this 800 ml pool was applied to a 105 ml Source Q column (Pfizer, Inc., N.Y., N.Y.). A 210 ml wash with buffer A was applied followed by a 1.0 L gradient from 0.05 M to 1.0 M NaCl in buffer A and fractions of 15 ml were collected. Fractions were assayed using the pNPP assay described above and the phosphatase activity eluted from 0.15-0.18 M NaCl. The remaining 700 ml of the Heparin Hyper-D pool was similarly applied and eluted; then the gradient fractions containing phosphatase activity were pooled.

The combined Source Q pool was dialyzed against buffer A and supplemented with 50% glycerol. Forty ml of this 120 ml pool was diluted to 500 ml with buffer A, then applied to a 400 ml PEI column (Whatman, Kent, U.K.) which had been pre-equilibrated with buffer A. A wash of 400 ml buffer A was applied followed by a linear gradient from 0.05 M to 1.0 M NaCl in buffer A and fractions of 15 ml were collected. Fractions were assayed using the pNPP assay described above. Phosphatase activity was eluted between 0.14 M and 0.2 M NaCl. The remaining 80 ml of the Source Q pool was similarly applied and eluted; then the gradient fractions containing phosphatase activity were pooled. This pool was dialyzed into storage buffer containing 10 mM Tris (pH 7.4), 1 mM $MgCl_2$, 1 mM DTT, 50% glycerol.

Example III

Determination of Optimal pH and Salt Conditions for Removal of a Phosphate Group by TAP Using TAP purified as described in Example II, the optimum conditions for removal of a phosphate group from DNA was determined. Dephosphorylation was measured by means of a phosphate release assay as follows: In a 50 μl reaction, two complementary 40mer oligonucleotides
5'-ACGTATGTTAGGTTAGGTTAGGTTAGGT-TAGGTTAGGCTC-3' (SEQ ID NO:1)
3'-TGCATACAATCCMTCCMTCCMTCCMTC-CAATCCGAG-5' (SEQ ID NO:2)

were annealed and end-labeled as recommended by the manufacturer using T4 polynucleotide kinase (New England Biolabs, Inc., Beverly, Mass.) and gamma $^{32}$P-ATP. This radioactive dimer was used to 'spike' 1 mg of a mixture of lambda HindIII fragments which served as a phosphatase substrate (20 μg/ml final). TAP activity was determined by release of radioactivity following incubation of the phosphatase with the substrate mix (0.01 pNPP units per reaction in a buffer containing 1 mM $MgCl_2$ and 0.1 mM $ZnCl_2$) at 37° C. for 5 minutes. Release was measured by precipitation of the DNA substrate with TCA and scintillation counting the radioactivity which was not precipitable. TCA precipitation consisted of adding 100 μl of Herring Sperm DNA (2 mg/ml) to each reaction as carrier. 150 μl of 20% cold TCA was then added. The samples were vortexed and chilled on ice for 5 minutes. Each reaction was centrifuged in a microfuge for 5 minutes at 14,000×g. 150 μL of each supernatant (50%) was added to 2 ml of scintillant and counted for 0.5 minutes. TAP activity was found to be linear over the range of 0.001 to 0.01 units measured by the pNPP calorimetric assay.

Figure 6:
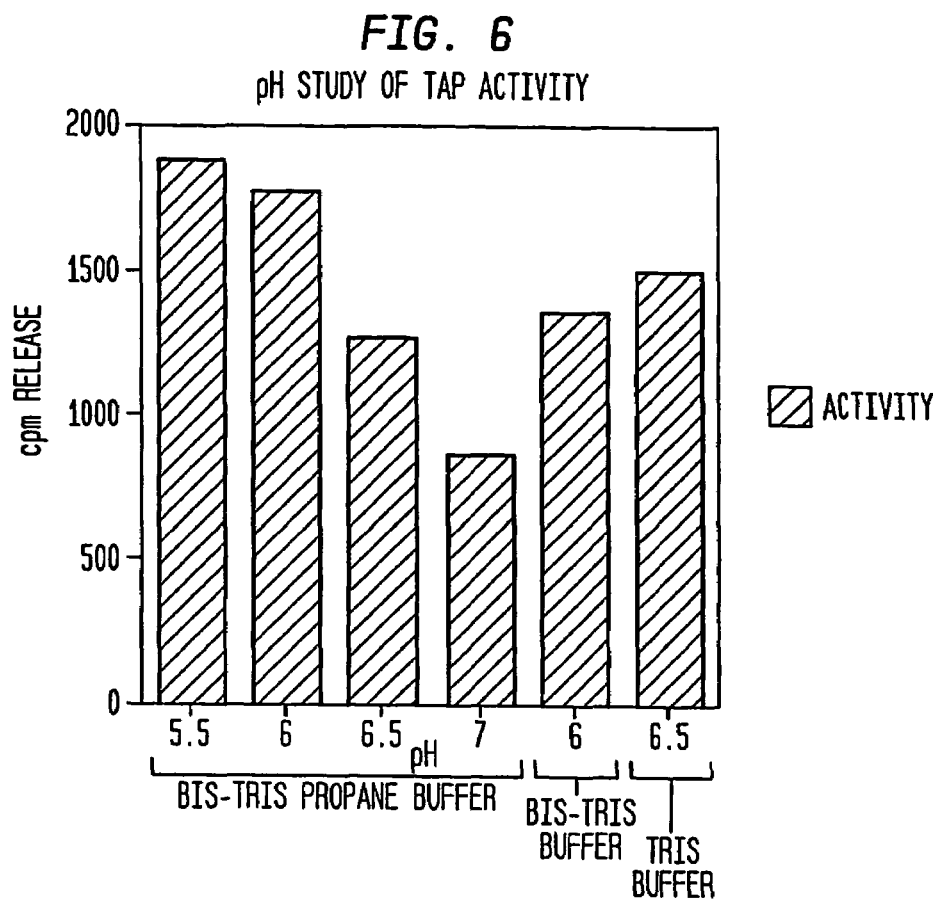
FIG. 6 shows a comparison of TAP activity at different pH and in different buffers. pH optimum was determined using the phosphate release assay. 50 mM of each buffer was incubated in a reaction mixture containing the $^{32}P$ labeled duplex DNA, 1 mM $MgCl_2$ and 0.1 mM $ZnCl_2$. The reaction was incubated at 37° C. for 5 minutes and the amount of trichloroacetic acid (TCA) soluble counts was measured.

A reaction buffer with a pH range of 5.5 to 9.5 was tested using three different buffers: Tris-HCL pH range 6 to 9.5, Bis-Tris Propane buffer pH range 6 to 7 and Bis-Tris Propane buffer pH range 5.5 to 7. The pH range which gave optimum activity on a DNA substrate in Bis-Tris Propane buffer proved to be between 5.5 and 6.0 (FIG. 6).

Figure 7:
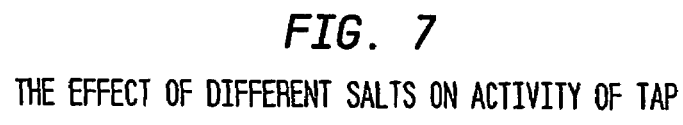
FIG. 7 shows the effect of different salts on the activity of TAP using the phosphate release assay. 100 mM of each salt, KCl, NaCl, potassium acetate or sodium acetate were tested.

The cation requirement was also tested. It was determined that contrary to Rina, et al., (supra (2000)) which reported that $Zn^{2+}$ ions were inhibitory in assays on pNPP, the assay described above revealed that the presence of $ZnCl_2$ gave a ten-fold increase phosphate release. 1 mM $MgCl_2$, 0.1 mM $ZnCl_2$ was subsequently included in TAP activity assays. Addition of other salts including KCl, NaCl, potassium acetate and sodium acetate at concentrations of 100 mM were observed to have no effect on TAP activity (FIG. 7).

Example IV

Determination of Thermolability of TAP

A unit of pNPP activity corresponds to the amount of enzyme required to hydrolyze 1 µmol of pNPP to p-nitrophenol in a reaction volume of 1 ml in 1 minute at room temperature. Ten pNPP units each of TAP, CIAP and SAP phosphatase were mixed with 1 µg lambda HindIII fragments in the recommended reaction buffer for each enzyme. The mixture was incubated at 37° C. for 10 minutes and then placed on ice. The reactions were then placed in a 65° C. water bath with samples removed and placed on ice after 5, 10, 20 and 30 minutes. Following heat treatment the samples were assayed for pNPP activity. Activity remaining was calculated as a percentage of the 0 time point. After 5 minutes the TAP had lost greater than 98% of its activity. In that same time period SAP still had 30% activity remaining and CIAP had almost 90% activity remaining. After 30 minutes SAP still had 20% activity remaining and CIP had 40% remaining showing that TAP is much more heat labile than either SAP or CIAP (FIG. 8).

Example V

Stability of TAP at 37° C. and 25° C.

Figure 9:
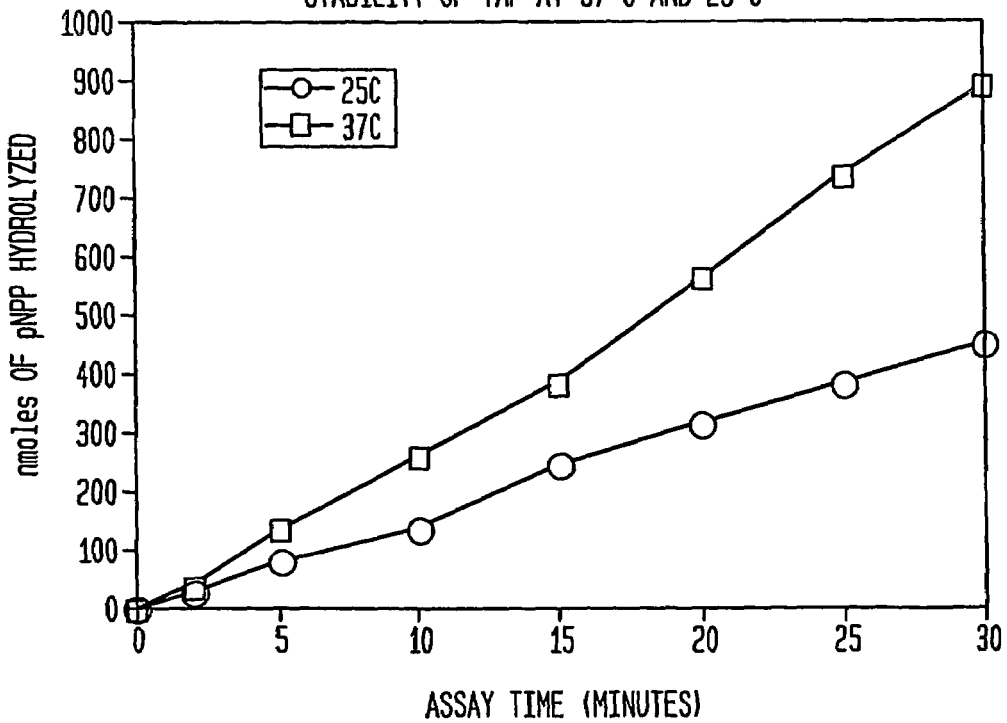
FIG. 9 shows the stability of TAP at 37° C. and 25° C. by measuring the release of phosphate from pNPP by TAP over time. Sample tubes containing 1 unit of TAP and unreacted pNPP were incubated at either 25° C. or 37° C. Reactions were stopped at 5-minute intervals for 0-30 minutes by adding NaOH to a final concentration of 5 N. Release of phosphate (accumulation of pNP) was measured by spectrophotometer at 405 nm (yellow) and graphed vs reaction time.

The stability of TAP activity at 37° C. and 25° C. was measured by release of free phosphate from pNPP in a colorimetric assay. Activity in this assay was determined by the generation of color that occurs when pNPP is converted to p-nitrophenol (pNP). A phosphatase reaction mix was prepared containing 1 M diethanolamine, (pH 8.5), 10 mM $MgCl_2$, 10 mM pNPP and 10 units TAP per ml. This mix was aliquoted to 3 ml reaction tubes, 0.1 ml per tube, and the reactions were initiated by placing the tubes at 25° C. or 37° C. Reactions were terminated at 5-minute intervals from 0-30 minutes by adding 0.1 ml of 10 N NaOH. Each reaction was diluted with 1 ml of reaction mix (without pNPP or TAP) to bring it to a suitable volume for spectrophotometry at 405 nm. Released phosphate was determined by measuring accumulated pNP and comparison to a known pNP standard. The results were expressed as nmoles phosphate released at either 25° C. or 37° C. over a 30 minute time course (FIG. 9). These results demonstrated that TAP activity is nearly two-fold higher at 37° C. than at 25° C. and that TAP is stable for at least 30 minutes at either temperature.

Example VI

Optimal Conditions for Storage of TAP

TAP was incubated at 75° C. for 5 minutes to determine optimum conditions for storage. Three different buffers were tested, Bis-Tris Propane buffer pH 6.0, Phosphate buffer pH 7.0 and Tris-HCL buffer pH 7.4, the latter proved the best at stabilizing the TAP. Different concentrations of NaCl were tested with no NaCl proving better than 50, 100 or 200 mM at maintaining enzyme activity. Where EDTA was inhibitory to TAP enzyme activity, both 1 mM DTT and 200 µg/ml BSA stabilized TAP activity. In a buffer containing Tris-HCL (pH 7.4), 1 mM $MgCl_2$, 1 mM DTT, 200 µg/ml BSA and 50% glycerol TAP was found to be stable for over 12 months with no decline in activity.

Example VII

Phosphatase Activity (a) Comparison of the Enzyme Activity of TAP to SAP in a DNA Ligation Assay Normalized for pNPP Activity:

Dephosphorylation of 5', 3' and blunt ends.

Efficiency is defined as the amount of DNA which can be dephosphorylated by 1 pNPP unit of enzyme based on the dilution which can dephosphorylate 1 µg of DNA.

SAP and TAP were both adjusted to 1 unit per µl using the pNPP assay. Litmus 28 DNA (New England Biolabs, Inc., Beverly, Mass.) was digested with either HindIII (5' overhang), EcoRV (blunt) or PstI (3' overhang). Aliquots of each cut vector DNA (1 mg/50 µl) were treated with several dilutions of each phosphatase for 30 minutes at 37° C. in their recommended buffers. TAP was heat killed for 5 minutes at 65° C. SAP was heat killed for 15 minutes at 65° C. Cut and dephosphorylated DNAs were then recircularized using the Quick Ligase Kit (New England Biolabs, Inc., Beverly, Mass.) according to the instructions. Ligated vectors were then transformed into *E. coli* and plated on ampicillin plates overnight. Phosphatase activity was considered complete if the number of colonies was less than 5% of the control (vector cut but not dephosphorylated). Whereas 1 pNPP unit of SAP could dephosphorylate 5 µg of 5' overhang DNA, the same number of pNPP units of TAP could dephosphorylate 50 µg of the same DNA (FIG. 10). TAP was therefore shown to be 10 times more efficient at removing phosphate groups from 5' overhangs on DNA. On blunt ends TAP was 50 times more efficient than SAP and on 3' overhangs TAP was 8 times more efficient.

(b) TAP can Remove Phosphate Groups from Deoxynucleotides.

The activity of TAP as a deoxynucleotidase was measured by release of free phosphate in a colorimetric assay essentially as described by Heinonen and Lahti (supra). Activity in this assay was determined relative to known phosphate standards. 0.1 ml of four different deoxynucleotide reaction mixes containing 50 mM Bis Tris-Propane (pH 6.0), 1 mM $MgCl_2$, 0.1 mM $ZnCl_2$ and 1 mM Sodium dATP, dCTP, dGTP or TTP were placed into four separate 1.5 ml tubes. 2.5 units of TAP were added to each tube. The reactions were initiated by placing the tubes at 37° C. and terminated after 15 minutes by placing the tubes at 65° C. for 5 minutes. The entire contents of each reaction mix tube (0.1 ml) was added to a glass tube containing 2.4 ml of measurement solution containing 1.25 N $H_2SO_4$, 4 mM Ammonium Molybdate and 50% acetone. The tube was vortexed briefly and incubated at room temperature for 15 minutes. The measurement reactions were stopped by adding citric acid to a final concentration of 0.33 M and the $OD_{390}$ of each tube was recorded. A standard curve was generated by adding 10 µl each of 0-30 mM phosphate standards to mock reaction tubes which were treated and measured identically to TAP reaction tubes. It was determined that dATP, dCTP, dGTP and TTP were nearly equivalent substrates for TAP; generating 1-2 nmoles of phosphate per minute per unit under these conditions.

Figure 11A:
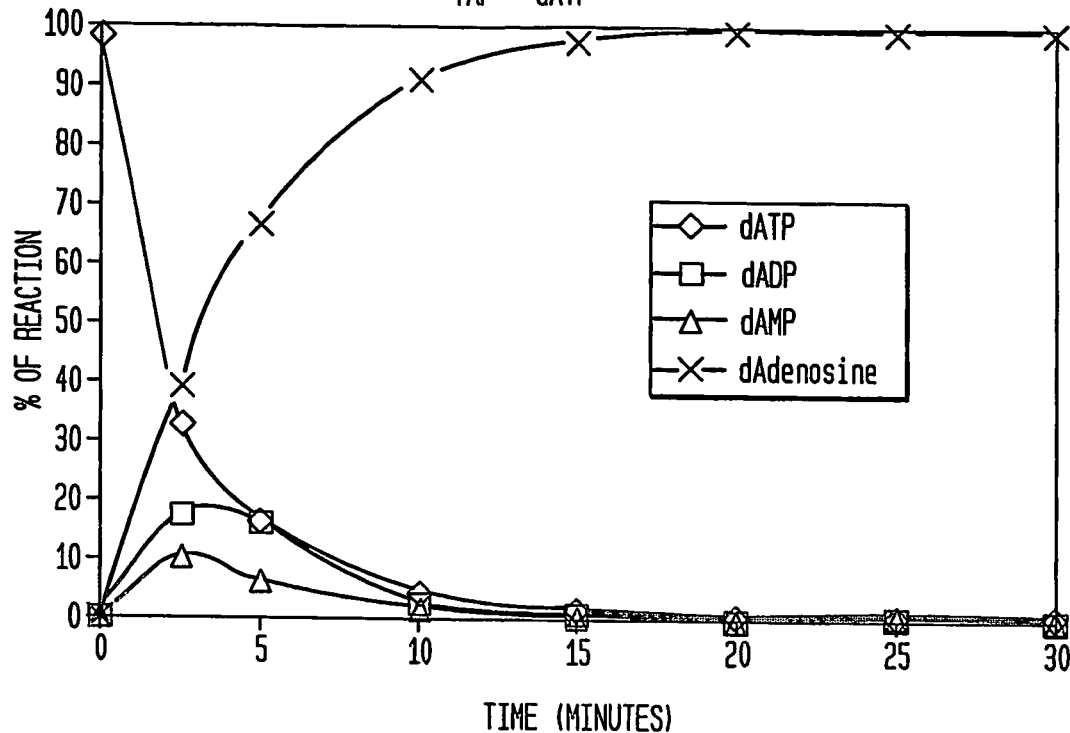
FIG. 11 shows the reaction time course of deoxynucleotidase activity for TAP and SAP. The composition of the dATPase reaction mixture was measured by Cap-HPLC at 5-minute intervals. The results are expressed for each component as a percentage of the total nucleotide present.
Figure 11B:
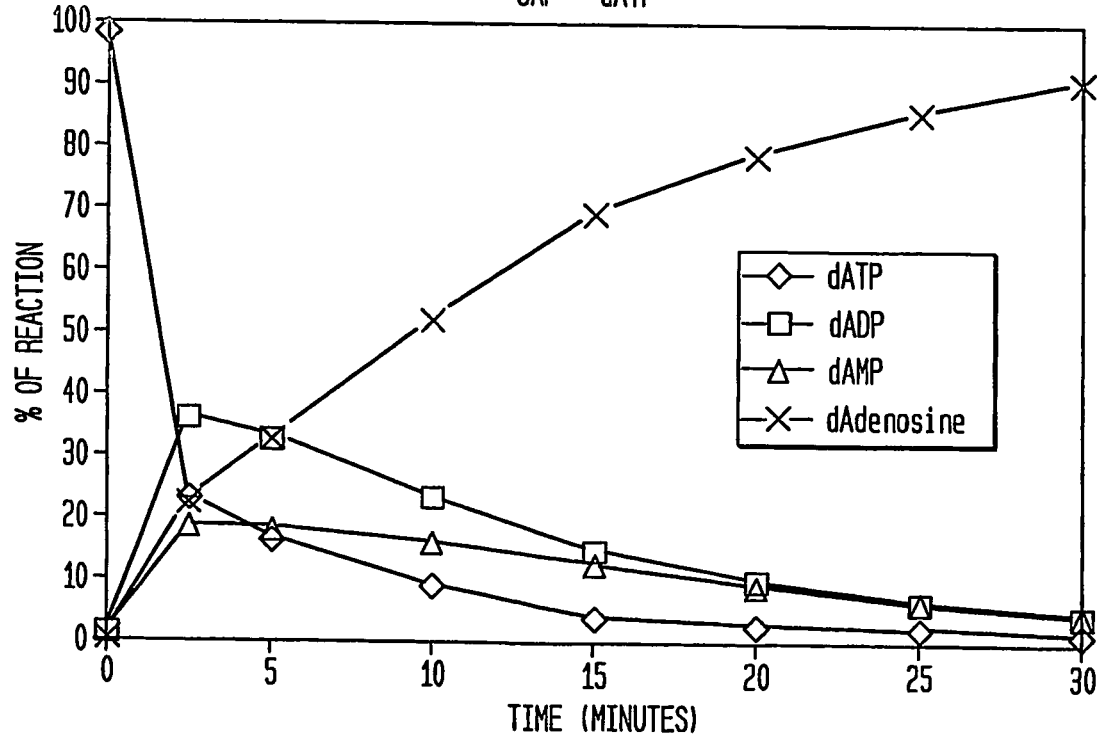

The deoxynucleotidase activities of SAP and TAP were compared. dATP was used as the test substrate, but it was concluded that similar results would be obtained using dCTP, dGTP or TTP. A deoxynucleotidase reaction mix was prepared containing 50 mM Bis Tris-Propane (pH 6.0), 1 mM $MgCl_2$, 0.1 mM $ZnCl_2$ and 0.8 mM dATP. 0.1 ml of this mix was aliquoted into seven 1.5 ml reaction tubes. 5 units of either TAP or SAP were added to each tube. The reaction was initiated by placing the tubes at 37° C. and terminated at 5-minute intervals for 0-30 minutes by placing the tubes at 65° C. for 5 minutes. Reaction products were subjected to capillary high-performance liquid chromatograph (Cap-HPLC) for a comparison to a profile containing standards for dATP, dADP, dAMP and deoxyadenosine. An Agilent 1100 Series Cap-HPLC equipped with an automated sample injector, column heater and a diode array detector was used to perform all analysis. Standards of dATP, dADP, dAMP and dA were purchased from Sigma Chemicals. A 3 μm, 150×1 mm C18 reverse-phase Cap-HPLC Develosil® column (Nomura Chemical Co. Ltd., Aichi, Japan) was used to separate the four species. An isocratic separation using 95% 0.1 M $K_2HPO_4$, pH 6.0 with KOH and 5% acetonitrile at a flow rate of 20 μl/min at 30° C. using a 100 μl flow sensor was found to produce a good resolution of all four species. Typical retention times for the dATP, dADP, dAMP and dA were 4.7, 5.2, 7.0 and 21.6 minutes, respectively. TAP-and SAP-treated samples were diluted to 0.2 ml in the above buffer and 4 μl were injected per run. Data was collected using Agilent ChemStation Software (Agilent Technologies, Palo Alto, Calif.) for the 254 nm and 280 nm absorbance and the peak sizes were quantitated by the software. The results were expressed for each reaction component as a percentage of the total nucleotide present (FIG. 11). These results demonstrated that TAP was capable of functioning as a deoxynucleotidase, removing phosphate groups from dNTP, dNDP or dNMP (where N represents adenosine, cytosine, guanosine or thymidine) and that TAP had a higher specific activity as a deoxynucleotidase than SAP (Heinonen and Lahti (supra)).

(c) TAP can Release Inorganic Phosphate from Pyrophosphate.

The activity of TAP as a pyrophosphatase was measured by release of free phosphate in a colorimetric assay essentially as described by Heinonen and Lahti (supra). Activity in this assay was determined relative to known phosphate standards using a known pyrophosphatase as a control. A pyrophosphatase reaction mix was prepared containing 50 mM Bis Tris-Propane (pH 6.0), 1 mM $MgCl_2$, 0.1 mM $ZnCl_2$ and 0.32 mM Sodium pyrophosphate. This mix was aliquoted to 1.5 ml reaction tubes, 0.5 ml per tube and serial 2-fold TAP dilution was performed, starting with 10 units in the first tube. The reaction was intitiated by placing the tubes at 37° C. and terminated after 10 minutes by placing the tubes at 65° C. for 5 minutes. The phosphate measurement solution was prepared containing 1.25 N $H_2SO_4$, 4 mM Ammonium Molybdate and 50% acetone. The entire contents of each reaction mix tube (0.5 ml) was added to a glass tube containing 2 ml of measurement solution, vortexed briefly and incubated at room temperature for 15 minutes. The measurement reactions were stopped by adding citric acid to a final concentration of 0.33 M and the $OD_{390}$ of each tube was recorded. A standard curve was generated by adding 10 μl each of 0-30 mM phosphate standards to mock reaction tubes which were treated and measured identically to TAP reaction tubes. A reaction containing TIPP was run in parallel. The TIPP reaction mix contained 2 units of TIPP, 50 mM Tricine (pH 8.0), 1 mM $MgCl_2$ and 0.32 mM Sodium pyrophosphate; and was incubated at 75° C. This reaction was stopped after 10 minutes by placing the tube at room temperature where TIPP is inactive. Measurement of released phosphate was performed as with TAP. This experiment showed that 10 units of TAP release approximately the same amount of inorganic phosphate as 2 units of TIPP (FIG. 12). These results demonstrate that TAP is capable of functioning as a pyrophosphatase, cleaving pyrophosphate (PPi) into inorganic phosphate (Pi).

(d) TAP Removes Phosphate Groups from Phosphorylated Peptides.

Preparation of $^{33}P$ labeled Myelin Basic Protein substrate (MyBP).

Serine/threonine (Ser/Thr) phosphorylated MyBP substrate was prepared using the Protein Serine/Threonine phosphatase (PSP) Assay System kit from New England Biolabs, Inc., Beverly, Mass. (catalog number #P0780S). Ser/Thr labeled MyBP substrate was diluted to a concentration of 50 μM (5× concentrated) with respect to the incorporated $^{33}P$.

Tyrosine (Tyr) phosphorylated MyBP substrate was prepared using the Protein Tyrosine phosphatase (PTP) Assay System kit from New England Biolabs, Inc., Beverly, Mass. (catalog number #P0785S). Tyr labeled MyBP substrate was diluted to a concentration of 25 μM (5× concentrated) with respect to the incorporated $^{33}P$.

10 μl of either Ser/Thr (50 μM) or Tyr labeled MyBP protein substrate (25 μM) was incubated with serial dilutions of the TAP phosphatase, 10 pNPP units of CIAP phosphatase or no enzyme in the recommended buffer for 1 hour at 37° C. The reactions were terminated by adding 200 μl of cold 20% TCA and incubating on ice for 5-10 minutes. The samples were then centrifuged at 12,000×g for 5 minutes. 150 μl of the supernatant is carefully removed and added to 2 mls of scintillation fluid and counted in a scintillation counter. The results are shown in FIG. 13.

The specific activity for TAP against phosphorylated Ser/Thr residues is 1910 nmol/min/mg which is slightly higher than the specific activity for CIAP against the same substrate. The specific activity for TAP against phosphorylated Tyr residues is also greater than the specific activity for CIAP (FIG. 13).

The results of the above experiment the activity of TAP were confirmed using three peptide substrates that each contained a single phospho-amino acid residue. These peptides were prepared using standard FMOC-chemistry. Peptide 1 contained a phosphoserine residue, Peptide 2 contained a phosphothreonine residue and Peptide 3 contained a phosphotyrosine residue indicated by pSer, pThr and pTyr, respectively. Listed below are the sequences for each peptide.

1. H-Val-Pro-Ile-Pro-Gly-Arg-Phe-Asp-Arg-Arg-Val-pSer-Val-Ala-Ala-Glu-$NH_2$ (SEQ ID NO:3)

2. H-Thr-Ala-Asp-Ser-Gln-His-Ser-pThr-Pro-Pro-Lys-Lys-Lys-Arg-Lys-Val-Glu-OH (SEQ ID NO:4)

3. H-Glu-Trp-Met-Arg-Glu-Asn-Ala-Glu-pTyr-Leu-Arg-Val-Ala-OH (SEQ ID NO:5)

Control peptides were also synthesized which had identical sequences but lacked the phosphate in each peptide.

A 50 ul reaction containing 5 ug of each phospho-peptide in 1×TAP buffer (see Example VIII) was incubated at 37° C. for 10 min with a serial dilution of TAP. After incubation Cap-HPLC was used to analyzed the samples. All three peptide de-phosphorylation reactions were analyzed using a Vydac Sum, C18 1×250 mm column at a flow rate of 25 µl/min. However an optimized gradient was required to separate the phosphorylated and dephosphorylated peptides for each peptide set. The Cap-HPLC gradient program timetables using an increasing percentage of acetonitrile (% B) relative to 0.1% TFA in water (v/v) were as follows:

TABLE 1

| Time (mins) | % B |
|---|---|
| Peptide 1 | |
| 0-10 | gradient from 20%-35% |
| 10-30 | gradient from 35-95% |
| Time | % B |
| Peptide 2 | |
| 0-10 | gradient from 8.5%-35% |
| 10-30 | gradient from 35%-95% |
| Peptide 3 | |
| 0-10 | gradient from 5%-25% |
| 10-30 | gradient from 25%-55% |
| 30-60 | gradient from 55%-95% |

Figure 14A:
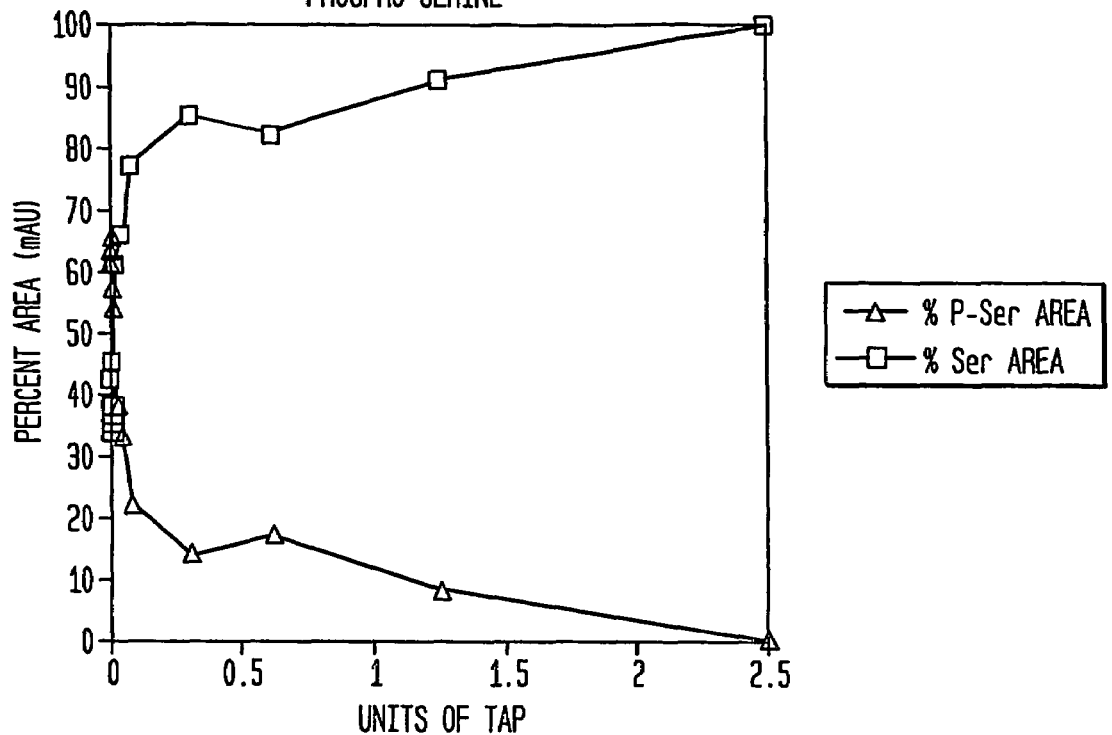
FIG. 14 shows the activity of TAP on three phospho-peptides:phospho-serine (graph A), phospho-threonine (graph B) and phospho-tyrosine (graph C) as measured by Cap-HPLC. The area of the absorbance peaks for the phospho-peptide and the peptide are measured and plotted on the graph as a percent of total area versus the number of units of TAP.
Figure 14B:
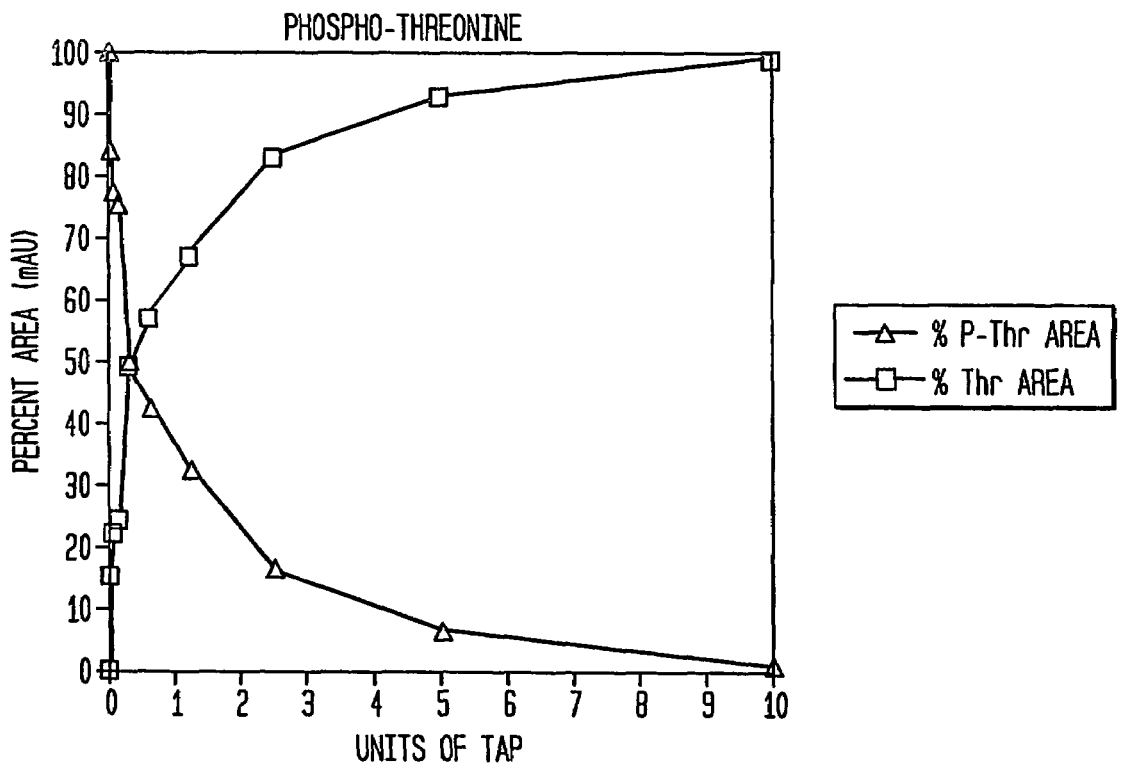
Figure 14C:
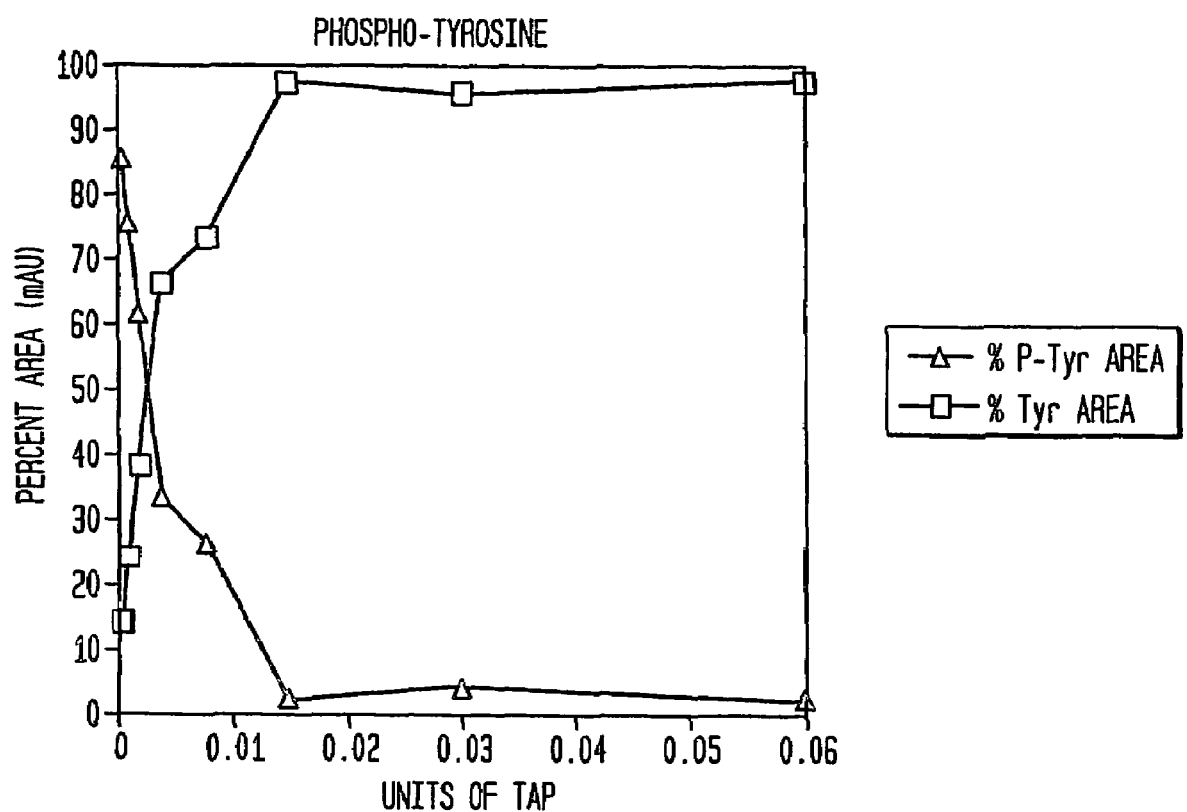

A ratio of 80% A and 20% B, 91.5% A and 8.5% B and 95% A and 5% B was used to equilibrate the column for peptides 1, 2 and 3 respectively. Data was collected using Agilent ChemStation Software (Agilent Technologies, Palo Alto, Calif.) for the 214 nm, 254 nm and 280 nm absorbances and the peak sizes were calculated by the software. To verify the identity of the species present in the reactions the reactions were also examined on Matrix-assisted laser desorption/ionization time-of-flight mass spectrometer (MALDI-TOF MS). An ABI Voyager DE Mass Spectrometer was used with α-cyano-4-hydroxycinnamic acid as the matrix, an accelerating voltage of 20 kV and a delay time of approximately 150 ηsec in positive ion mode. FIG. 14 consists of three graphs of the compiled data showing the decreased amount of the phospho-peptide and increasing amount of dephosphorylated peptide with increasing amounts of TAP. This data shows that TAP is most active on the phospho-tyrosine peptide with only 0.02 units of enzyme being required to remove all the phosphates from 5 µg of the peptide in 10 mins. 2.5 units and 10 units of TAP were required to completely remove the phosphates from the phospho-serine and phospho-threonine peptides respectively. This data shows that TAP can be used to remove phosphate groups from peptides.

Example VIII

Figure 15:
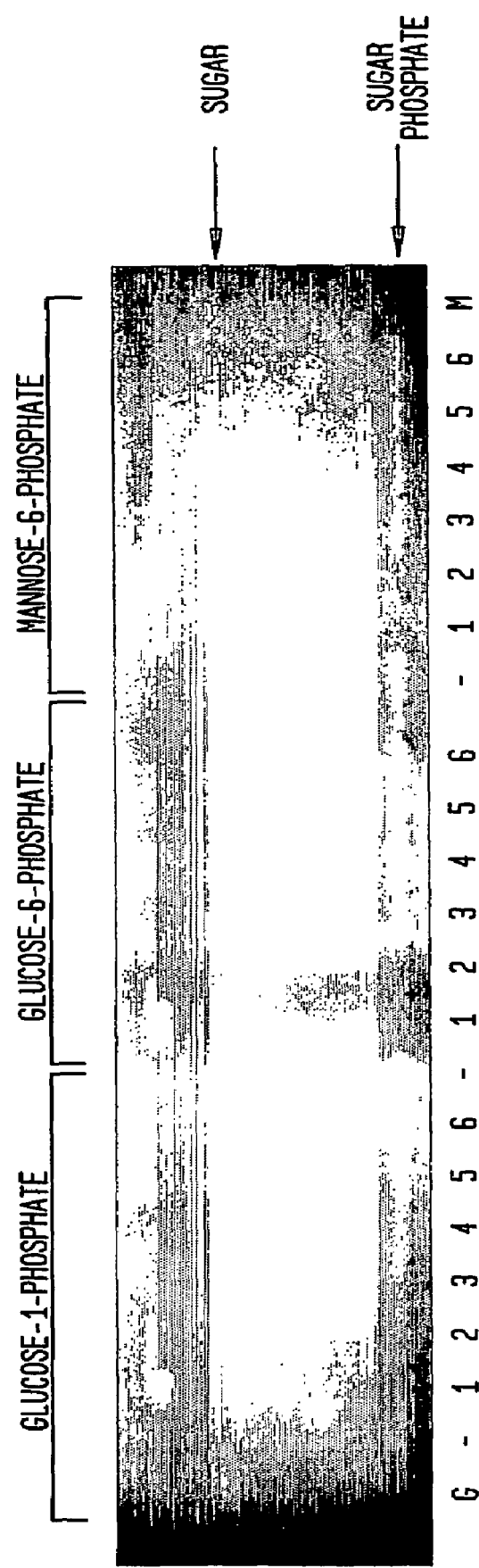
FIG. 15 shows TLC analysis of a titer of TAP on three different sugar-phosphates, glucose-1-phosphate, glucose-6-phosphate and mannose-6-phosphate. 3 µg pf Glucose (G) and mannose (M) were spotted as positive controls. Negative controls (-) contain just the reaction mix containing buffer and the sugar phosphate substrate incubated without enzyme. Lanes marked 1 through 6 are the serial dilution (1:1) of the enzyme in the reaction mix starting with reaction 1 containing 12.5 units of TAP down to reaction 6 containing 0.4 units of TAP. Arrows indicate the distances that the sugars and the sugar-phosphates migrate on the TLC.

TAP can Dephosphorylate Sugar Phosphates Regardless of the Position of the Phosphate on the Sugar To test if TAP could cleave the phosphate residue from a sugar phosphate irrespective of position, its activity for three sugar phosphates glucose-1-phosphate, glucose-6-phosphate and mannose-6-phosphate was determined. A dilution series of the reaction mixture was prepared for each sugar phosphate where each reaction mixture contained 100 µl of the 5 mg/ml solution of one of the sugar phosphates, 30 µl of the 10×TAP Buffer (500 mM Bis Tris-Propane, 10 mM $MgCl_2$, 1 mM $ZnCl_2$, pH 6.0) and 210 µl $H_2O$. 50 µl of the reaction mix was added to the first tube and 25 µl of the reaction mix to five subsequent tubes. This was repeated for each of the three sugar phosphates to be tested. These tubes were placed on ice and allowed to chill. Once cold 5 µl of the TAP (5 U/µl) was added to the first tube containing 50 µl reaction mix. After mixing 25 µl was removed from this tube and placed in the next tube which contained 25 µL of the reaction mix. After mixing 25 µl was removed from this second tube and placed in the next tube. This 1:1 dilution series was continued for a total of 6 tubes. After a dilution series of the TAP had been prepared for each sugar phosphate, the tubes were removed from the ice and placed at 37° C. for 15 minutes. After incubation 3 µl of each sample was spotted in a tight band on silica gel glass backed thin layer chromatography (TLC) plate. Negative controls containing just the mix incubated with no enzyme and positive controls containing 1 mg/ml glucose or mannose were also spotted on the TLC. The spots were completely dried with a hot air gun (temperature not exceeding 70° C.). The plate was developed until the solvent front moved 9 cm in isopropanol, ethanol and water (2.5:1:0.5 v:v:v). Following chromatography, the plate was dried and sprayed with 10% perchloric acid. The sugars were visualized by charring the plate with a heat gun. Increased sensitivity was achieved by visualizing the products under UV at 366 nm. Complete digestion of 42 µg of glucose-1-phosphate, glucose-6-phosphate and mannose-6-phosphate was achieved in 15 minutes at 37° C. using 6 U of TAP (FIG. 15).

The linkage of the phosphate on the sugar (i.e. 1 or 6) had no apparent effect on the activity of the enzyme. In addition the activity of the TAP on mannose sugar phosphates was the same as on glucose sugar phosphates.

What is claimed is:

1. A method of dephosphorylating a phosphorylated substrate, comprising:
   (a) adding the thermolabile Antarctic phosphatase (TAP) of SEQ ID NO: 10 to the substrate in a buffer at pH 5.5-6.5; and
   (b) incubating the mixture comprising the substrate and the TAP under conditions to allow phosphate to be removed from the substrate.

* * * * *

UNITED STATES PATENT AND TRADEMARK OFFICE
CERTIFICATE OF CORRECTION

PATENT NO. : 7,319,014 B2  
APPLICATION NO. : 10/545905  
DATED : January 15, 2008  
INVENTOR(S) : Jack S. Benner, II et al.

Page 1 of 1

It is certified that error appears in the above-identified patent and that said Letters Patent is hereby corrected as shown below:

At column 1, line number 39, delete "0441252" and insert -- 0441752 --, therefor.

At column 10, line number 55, delete "µL" and insert -- µl --, therefor.

At column 14, line number 35, delete "mis" and insert -- mls --, therefor.

At column 15, line number 3, delete "Sum" and insert -- 5µm --, therefor.

At column 16, line number 24, delete "µL" and insert -- µl --, therefor.

Signed and Sealed this  
Tenth Day of May, 2011

David J. Kappos  
*Director of the United States Patent and Trademark Office*

SEQUENCE LISTING

```
<160> NUMBER OF SEQ ID NOS: 10

<210> SEQ ID NO 1
<211> LENGTH: 40
<212> TYPE: DNA
<213> ORGANISM: unknown
<220> FEATURE:
<223> OTHER INFORMATION: random substrate used in an assay

<400> SEQUENCE: 1
```

-continued

```
acgtatgtta ggttaggtta ggttaggtta ggttaggctc                              40
```

<210> SEQ ID NO 2
<211> LENGTH: 40
<212> TYPE: DNA
<213> ORGANISM: unknown
<220> FEATURE:
<223> OTHER INFORMATION: random substrate used in an assay

<400> SEQUENCE: 2

```
tgcatacaat ccaatccaat ccaatccaat ccaatccgag                              40
```

<210> SEQ ID NO 3
<211> LENGTH: 16
<212> TYPE: PRT
<213> ORGANISM: Bovine adenovirus type 2
<220> FEATURE:
<221> NAME/KEY: MOD_RES
<222> LOCATION: (12)..(12)
<223> OTHER INFORMATION: At the location 12, Serine was modified with a
      single phospho-amino acid

<400> SEQUENCE: 3

Val Pro Ile Pro Gly Arg Phe Asp Arg Arg Val Ser Val Ala Ala Glu
1               5                   10                  15

<210> SEQ ID NO 4
<211> LENGTH: 17
<212> TYPE: PRT
<213> ORGANISM: unknown
<220> FEATURE:
<223> OTHER INFORMATION: Polyomavirus BK
<220> FEATURE:
<221> NAME/KEY: MOD_RES
<222> LOCATION: (8)..(8)
<223> OTHER INFORMATION: At the location 8, Threonine was modified by a
      single phospho-amino acid

<400> SEQUENCE: 4

Thr Ala Asp Ser Gln His Ser Thr Pro Pro Lys Lys Lys Arg Lys Val
1               5                   10                  15

Glu

<210> SEQ ID NO 5
<211> LENGTH: 13
<212> TYPE: PRT
<213> ORGANISM: unknown
<220> FEATURE:
<223> OTHER INFORMATION: Human TFIIIB
<220> FEATURE:
<221> NAME/KEY: MOD_RES
<222> LOCATION: (9)..(9)
<223> OTHER INFORMATION: At the location 9, Tyrosine was modified by a
      0single phospho-amino acid

<400> SEQUENCE: 5

Glu Trp Met Arg Glu Asn Ala Glu Tyr Leu Arg Val Ala
1               5                   10

<210> SEQ ID NO 6
<211> LENGTH: 60
<212> TYPE: DNA
<213> ORGANISM: unknown
<220> FEATURE:
<223> OTHER INFORMATION: unidentified Antarctic organism

<400> SEQUENCE: 6

```
cccccccata tgcatcatca tcatcatcat gtaaaaaatg agcctcaatt aaaaacaccc       60
```

<210> SEQ ID NO 7
<211> LENGTH: 17
<212> TYPE: PRT
<213> ORGANISM: unknown
<220> FEATURE:
<223> OTHER INFORMATION: unidentified Antarctic organism
<220> FEATURE:
<221> NAME/KEY: MISC_FEATURE
<222> LOCATION: (10)..(58)
<223> OTHER INFORMATION: N-terminal amino acid sequence

<400> SEQUENCE: 7

Met His His His His His His Val Lys Asn Glu Pro Gln Leu Lys Thr
1               5                   10                  15
Pro

<210> SEQ ID NO 8
<211> LENGTH: 31
<212> TYPE: DNA
<213> ORGANISM: unknown
<220> FEATURE:
<223> OTHER INFORMATION: unidentified Antarctic organism

<400> SEQUENCE: 8
gtcaggtctt agctcgagtt attgattcca c                                        31

<210> SEQ ID NO 9
<211> LENGTH: 1140
<212> TYPE: DNA
<213> ORGANISM: unknown
<220> FEATURE:
<223> OTHER INFORMATION: Thermobile Antarctic Phosphatase

<400> SEQUENCE: 9
atgaagctta aaaaaattgt ttttacccta atcgcattag gtctattttc ttgcaaaaca          60
acaagtgttt tagtaaaaaa tgagcctcaa ttaaaaacac ccaaaaatgt tattctgtta        120
attagtgatg gcgcaggatt atcacaaatt tcatctacct tttatttttaa agagggtact       180
ccaaactaca cacagtttaa aaatattggc ttgataaaaa catcctcttc cagagaagat        240
gtaactgatt cagcctctgg cgctactgct ttttcctgtg gtattaaaac atataatgcg        300
gcaattggtg ttgctgatga ttcaactgct gtaaaaagca ttgtggaaat tgcagcatta        360
aacaacatta aaacaggagt tgttgcaacg tcctccatta cacatgctac gcctgcaagt        420
ttttatgccc atgctttaaa cagaggccta gaagaagaaa ttgcgatgga tatgacggaa        480
tctgatctag actttttttgc tggaggcggt ttaaactact ttaccaagcg taaagacaaa       540
aaagatgttt tagctatttt aaaaggaaat caatttacca taaatactac tggattaaca         600
gatttttcaa gcattgcatc aaatagaaaa atgggttttt tattagcgga tgaagccatg        660
cctactatgg aaaaaggaag aggtaatttt ctatccgcag caacagattt agccattcag        720
tttttaagta aagacaattc agcgttcttt attatgagcg aaggttctca aatagattgg        780
ggtggccatg caaataatgc atcctattta atttctgaaa ttaatgattt tgacgatgcc        840
attggcactg ctttggcttt cgctaaaaaa gatggtaata cattggttat tgtaacttct        900
gaccatgaaa ctgagggttt tacattggct gccaaaaaaa ataaaagaga gatggtagt        960
gagtatagtg attatacaga gatcggacct acttttttcta ctggagggca ttctgcaacc     1020
ttaattcctg tttttgctta cggccctgga tcagaagaat ttattggaat ctatgaaaac     1080
aatgaaattt ttcataaaat attaaaagtg acaaagtgga atcaataaac ataactaaga     1140

<210> SEQ ID NO 10
<211> LENGTH: 375
<212> TYPE: PRT
<213> ORGANISM: unknown
<220> FEATURE:
<223> OTHER INFORMATION: Thermolabile Antarctic Phosphatase

<400> SEQUENCE: 10

```
Met Lys Leu Lys Lys Ile Val Phe Thr Leu Ile Ala Leu Gly Leu Phe
 1               5                  10                  15

Ser Cys Lys Thr Thr Ser Val Leu Val Lys Asn Glu Pro Gln Leu Lys
            20                  25                  30

Thr Pro Lys Asn Val Ile Leu Leu Ile Ser Asp Gly Ala Gly Leu Ser
        35                  40                  45

Gln Ile Ser Ser Thr Phe Tyr Phe Lys Glu Gly Thr Pro Asn Tyr Thr
 50                  55                  60

Gln Phe Lys Asn Ile Gly Leu Ile Lys Thr Ser Ser Arg Glu Asp
 65                  70                  75                  80

Val Thr Asp Ser Ala Ser Gly Ala Thr Ala Phe Ser Cys Gly Ile Lys
                85                  90                  95

Thr Tyr Asn Ala Ala Ile Gly Val Ala Asp Asp Ser Thr Ala Val Lys
            100                 105                 110

Ser Ile Val Glu Ile Ala Ala Leu Asn Asn Ile Lys Thr Gly Val Val
        115                 120                 125

Ala Thr Ser Ser Ile Thr His Ala Thr Pro Ala Ser Phe Tyr Ala His
130                 135                 140

Ala Leu Asn Arg Gly Leu Glu Glu Ile Ala Met Asp Met Thr Glu
145                 150                 155                 160

Ser Asp Leu Asp Phe Phe Ala Gly Gly Gly Leu Asn Tyr Phe Thr Lys
                165                 170                 175

Arg Lys Asp Lys Lys Asp Val Leu Ala Ile Leu Lys Gly Asn Gln Phe
            180                 185                 190

Thr Ile Asn Thr Thr Gly Leu Thr Asp Phe Ser Ser Ile Ala Ser Asn
        195                 200                 205

Arg Lys Met Gly Phe Leu Leu Ala Asp Glu Ala Met Pro Thr Met Glu
210                 215                 220

Lys Gly Arg Gly Asn Phe Leu Ser Ala Ala Thr Asp Leu Ala Ile Gln
225                 230                 235                 240

Phe Leu Ser Lys Asp Asn Ser Ala Phe Phe Ile Met Ser Glu Gly Ser
                245                 250                 255

Gln Ile Asp Trp Gly His Ala Asn Asn Ala Ser Tyr Leu Ile Ser
            260                 265                 270

Glu Ile Asn Asp Phe Asp Asp Ala Ile Gly Thr Ala Leu Ala Phe Ala
        275                 280                 285

Lys Lys Asp Gly Asn Thr Leu Val Ile Val Thr Ser Asp His Glu Thr
290                 295                 300

Gly Gly Phe Thr Leu Ala Ala Lys Lys Asn Lys Arg Glu Asp Gly Ser
305                 310                 315                 320

Glu Tyr Ser Asp Tyr Thr Glu Ile Gly Pro Thr Phe Ser Thr Gly Gly
                325                 330                 335

His Ser Ala Thr Leu Ile Pro Val Phe Ala Tyr Gly Pro Gly Ser Glu
            340                 345                 350

Glu Phe Ile Gly Ile Tyr Glu Asn Asn Glu Ile Phe His Lys Ile Leu
        355                 360                 365
```

```
-continued

Lys Val Thr Lys Trp Asn Gln
    370                 375
```